(12) United States Patent
Kessler et al.

(10) Patent No.: US 9,222,067 B2
(45) Date of Patent: Dec. 29, 2015

(54) SINGLE USE CENTRIFUGE SYSTEM FOR HIGHLY CONCENTRATED AND/OR TURBID FEEDS

(71) Applicant: Pneumatic Scale Corporation, Cuyahoga Falls, OH (US)

(72) Inventors: Stephen B Kessler, Princeton, MA (US); T. David Marro, Magnolia, MA (US)

(73) Assignee: PNEUMATIC SCALE CORPORATION, Cuyahoga Falls, OH (US)

( * ) Notice: Subject to any disclaimer, the term of this patent is extended or adjusted under 35 U.S.C. 154(b) by 474 days.

(21) Appl. No.: 13/684,051

(22) Filed: Nov. 21, 2012

(65) Prior Publication Data

US 2013/0089917 A1    Apr. 11, 2013

Related U.S. Application Data

(63) Continuation-in-part of application No. 12/676,273, filed on Mar. 3, 2010.

(60) Provisional application No. 61/562,438, filed on Nov. 21, 2011, provisional application No. 61/125,033, filed on Apr. 22, 2008.

(51) Int. Cl.
  *C12M 1/00* (2006.01)
  *C12N 1/02* (2006.01)
  *B04B 5/04* (2006.01)

(52) U.S. Cl.
  CPC .............. *C12M 47/02* (2013.01); *C12N 1/02* (2013.01); *B04B 5/0442* (2013.01); *B04B 2005/0464* (2013.01)

(58) Field of Classification Search
  CPC ................. C12M 47/02; B04B 5/0442; B14B 2005/0464
  See application file for complete search history.

(56) References Cited

U.S. PATENT DOCUMENTS

| 5,160,309 | A  * | 11/1992 | Robertsson ..................... 494/43 |
| 2002/0020679 | A1 * | 2/2002 | Jorgensen et al. ............. 210/781 |
| 2007/0267360 | A1 * | 11/2007 | Pham ........................... 210/787 |

FOREIGN PATENT DOCUMENTS

| EP | 0257755 A1 | 3/1988 |
| WO | 94/08721 A1 | 4/1994 |
| WO | 01/76759 A1 | 10/2001 |
| WO | 2005/016544 A1 | 2/2005 |

\* cited by examiner

*Primary Examiner* — Jonathan Hurst
(74) *Attorney, Agent, or Firm* — Ralph E. Jocke; Walker & Jocke

(57) ABSTRACT

A method and apparatus for cell harvest of production scale quantities of cell cultures using single use components comprising a flexible membrane mounted on a rigid frame and is supported within a multiple use rigid centrifuge bowl, such single use components including a core with an increased diameter and an internal truncated cone shape in order to permit the system to maintain a sufficiently high angular velocity to create a settling velocity suited to efficiently processing highly concentrated cell culture streams. Features which minimize feed turbidity, and others which permit the continuous or semi-continuous discharge of cell concentrate, increase the overall production rate over the rate which can be achieved using current intermittent processing methods for large cell culture volumes. Injection of a diluent during the cell concentrate removal process permits more complete removal of viscous cell concentrates.

20 Claims, 15 Drawing Sheets

SINGLE USE CENTRIFUGE SYSTEM FOR HIGHLY CONCENTRATED AND/OR TURBID FEEDS

CROSS-REFERENCE TO RELATED APPLICATIONS

This application is a continuation-in-part of application Ser. No. 12/676,273, filed Mar. 3, 2010, and which claims priority to U.S. Provisional Application Ser. No. 61/562,438, filed Nov. 21, 2011.

BACKGROUND OF THE INVENTION

Within the field of cell culture as applied to bio-pharmaceutical processes there exists a need to separate cells from the media in which they are grown. The desired product from the cell culture may be a molecular species that the cell excretes into the media, a molecular species that remains within the cell, or it may be the cell itself. At production scale, the initial stages of cell culture process typically take place in bioreactors, which may be operated in either batch or continuous mode. Intermediate variations such as repeat batch are practiced as well. In all cases the product must eventually be separated from other process components prior to final purification and product formulation. Cell harvest is a general term applied to these cell separations. Clarification is a term denoting separations wherein a cell-free supernatant (or centrate) is the objective. Cell recovery is a term often applied to separations wherein a cell concentrate is the objective. The present invention is directed to cell harvest separations in large-scale cell culture systems.

Methods currently in common use for cell harvest separations include batch, intermittent, continuous and semi-continuous centrifugation, tangential flow filtration (TFF) and depth filtration. Historically, centrifuges for cell harvest of large volumes of cell culture at production scale are complex multiple use systems that require clean-in-place (CIP) and steam-in-place (SIP) technology to provide an aseptic environment to prevent contamination by microorganisms. At lab scale and for continuous cell harvest processes, smaller systems are currently in use. These smaller lab scale systems are based on pre-sterilized, single-use fluid path components.

Pre-sterilized, single-use components are already used for media storage, mix tanks, hold tanks, and bioreactors, e.g. up to about 2000 liter capacity which are used in the initial stages of the cell culture process, but until recently there were no production scale centrifuges available that used pre-sterilized components for the harvest of such large cell culture batches. The UniFuge centrifuge system, manufactured by Pneumatic Scale Corporation, described in published application US 2010/0167388, the entire disclosure of which is incorporated herein by reference, overcomes such limitations, and successfully processes culture batches in the range of 3-30 liters/minute in quantities of up to about 2000 liters using intermittent processing. Intermittent processing requires periodically stopping both rotation of the centrifuge bowl and the feed flow in order to discharge concentrate. This works well with lower concentration, high viability cultures, in which large batches can be processed, and the cell concentrate discharged relatively quickly and completely.

The current industry trend is toward harvesting highly concentrated and/or low viability cell cultures, which contain a high concentration of cells and cell debris in the feed, sometimes referred to as "high turbidity feeds." Such high turbidity feeds slow down the processing rate using current technology, because:

1. a slower feed flow rate is required to provide increased residence time in the centrifuge in order to separate small cell debris particles, and
2. the higher concentrations of both cells and cell debris result in the bowl filling rapidly with cell concentrate, which require the bowl to be stopped frequently to discharge concentrate.

These combined factors result in a greatly reduced net throughput rate, and unacceptably long cell harvest processing times. In addition to the increased costs which are associated with a longer processing time, increased time in the centrifuge may also result in a higher degree of product contamination and loss when harvesting low viability cell cultures.

This high concentration of cell and cell debris also results in a cell concentrate with a very high viscosity, which makes it more difficult to completely discharge the cell concentrate, even with a prolonged discharge cycle. In some cases, an additional buffer rinse cycle must be added to obtain a sufficiently complete discharge of concentrate. The need to make either or both of these adjustments to the discharge cycle further increases the processing time, making the challenges of processing a large volume of cell culture more complex and costly.

Scaling up the existing technology, by increasing the bowl size to increase the length of the feeding portion of the intermittent processing cycle is not practical because it would also result in a proportionately longer discharge cycle for the cell concentrate. Another limitation that precludes simple geometric scale-up is variation in scaling of the pertinent fluid dynamic factors. The maximum processing rate of any centrifuge depends on the settling velocity of the particles being separated. The settling velocity is given by a modification of Stokes' law defined by Equation 1:

$$v = \frac{\Delta\rho \cdot r \cdot d^2 \cdot \omega^2}{18 \cdot \mu} \qquad \text{Equation 1}$$

where v=settling velocity, $\Delta\rho$ is solid-liquid density difference, d is particle diameter, r is radial position of the particle, $\omega$ is angular velocity, and $\mu$ is liquid viscosity. With respect to scale-up geometry, the radius of the bowl affects the maximum radial position r that particles can occupy. Therefore, if the other parameters in Equation 1 are held constant, an increase in bowl radius leads to an increase in average settling velocity and a gain in throughput for a given separation efficiency. However, as the radius increases it becomes more difficult to maintain the angular velocity of the bowl because of the material strength that would be required, and other engineering limitations. If a decrease in angular velocity is larger than the square root of the proportional increase in radius, then the average settling velocity and the gain in throughput (which is proportional to radius) both decline.

One of the engineering limitations that must be considered is that the angular velocity needed to rotate the larger bowl is not be practical to achieve because of the massive and costly centrifuge drive platform that would be needed.

In addition if the angular velocity is held constant as the radius increases, the forces urging the cells toward the walls of the centrifuge also increase. When the bowl is rotated at sufficiently high angular velocity to create the desired processing efficiency the walls of the container and the cells which accumulate there experience added stress. As to the cells, this can cause cell damage by packing the cells to excessively high concentrations. Cell damage is a drawback in applications wherein cell viability needs to be maintained and can lead to contamination of products that are present in solution in the centrate. The higher viscosity resulting from excessively high cell concentrations is a drawback for complete discharge of the cell concentrate.

Accordingly, there is a need for a centrifuge system, with single use components, which can be used to efficiently separate production scale quantities of cell cultures having a high concentration of cells and cell debris.

SUMMARY OF THE INVENTION

The present invention comprises apparatus and methods for centrifugal separation of cells in large-scale cell culture with a high cell concentration using pre-sterilized, single-use fluid path components. The centrifuges discussed herein use a pre-sterilized, single-use design, and are capable of processing cell suspensions, with high cell concentrations, at flow rates in the range of about 2 to about 40 liters per minute, preferably about 5 to about 20 liters per minute.

The foregoing are accomplished in embodiments of the invention using rotationally fixed feed and discharge components. Single use components comprising a flexible membrane mounted on a rigid frame including a core with an enlarged diameter are supported within a multiple use rigid bowl having an internal truncated cone shape. These structures permit the system to maintain a sufficiently high angular velocity to create a settling velocity suited to efficiently processing highly concentrated cell culture streams. Features which minimize feed turbidity, and others which permit the continuous or semi-continuous discharge of cell concentrate, increase the overall production rate over the rate which can be achieved using current intermittent processing methods for large cell culture volumes. Injection of a diluent during the cell concentrate removal process permits more complete removal of viscous cell concentrates. Diluents are disclosed that are particularly advantageous for specific types of feed streams.

DETAILED DESCRIPTION OF THE INVENTION

The present invention comprises apparatus and methods for continuous or semi-continuous centrifugal separation of low viability cell suspension cultures containing a high concentration of cells and cell debris, at a rate suitable for processing large volumes of cell suspensions on a commercial scale. The centrifuges of the present invention are of pre-sterilized, single-use design and are capable of processing such cell suspensions at flow rates exceeding 20 liters per minute. This flow capacity enables total run times in the range of 2 to 3 hours for a 2000 liter bioreactor. More preferably, the single-use centrifuge systems are capable of processing about 300 to 2,000 liters of fluid while operating at a rate of about 2 to 40 liters per minute.

Figure 1:
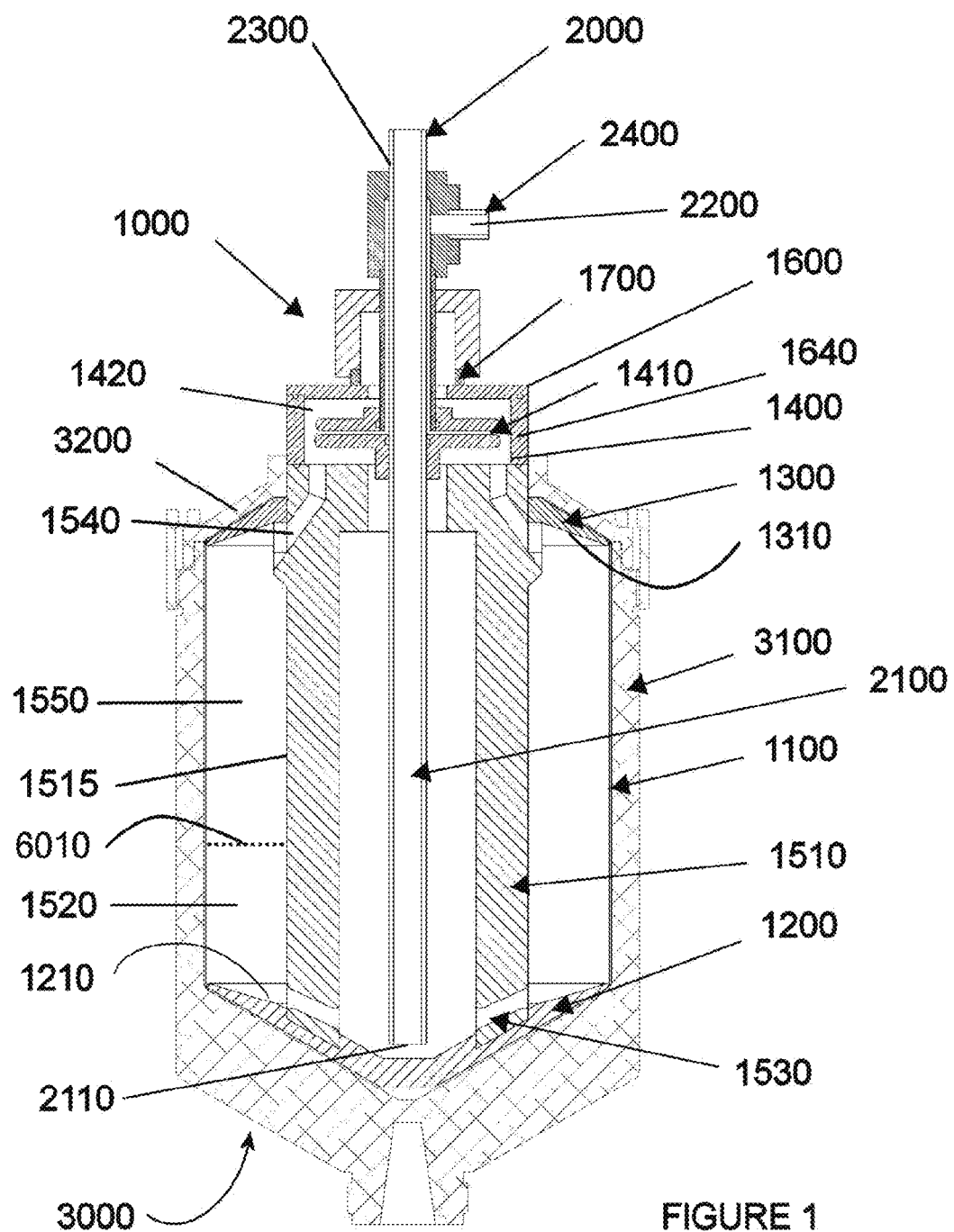
FIG. 1 is a schematic view of an embodiment of a centrifuge system including single use and multiple use components.

FIG. 1 discloses single use centrifuge structure 1000. The centrifuge structure 1000 includes a core structure 1500 (best seen in FIG. 3) comprising a core 1510, upper flanges 1300, lower flanges 1200, and a flexible liner 1100 sealed to both an upper flange 1300 and a lower flange 1200. The centrifuge structure 1000 also includes a centripetal pump 1400, comprising a pair of stationary paring disks 1410 in a rotating pump chamber 1420, and a rotating mechanical seal 1700.

Centrifuge structure 1000 also includes a feed/discharge assembly 2000. The assembly 2000 comprises a plurality of concentric tubes about the axis 1525 (labeled in FIG. 12) of the centrifuge 1000. The innermost portion of feed/discharge assembly 2000 includes a feed tube 2100. A plurality of additional tubes concentrically surround the feed tube 2100, and may include tubes or fluid pathways to permit centrate discharge 2200, concentrate discharge 2500 (see, for example, FIG. 12), or diluent feed 5000 (see, for example, FIG. 12). Each portion of the feed/discharge connection may be in fluid connection with a portion of the interior of the centrifuge 1000, and a collection or feed chamber (not shown) via appropriate fluid connections, and may include further tubes which are in fluid connection with the concentric tubes to remove or add the centrate, concentrate, or diluents from or to the system.

The upper and lower flanges 1300, 1200, as illustrated in FIG. 1, comprise conical bowls, axially aligned with and concave toward the core 1510. Core 1510 comprises a generally cylindrical body with a hollow cylindrical center large enough to accept feed tube 2100 having an axis 1525 (labeled in FIG. 12). The upper flange 1300, the core 1510 and the lower flange 1200 may be a unitary structure to provide a stronger support structure for flexible liner 1100. In other embodiments, the core structure 1500 may be formed from a plurality of component parts. In further embodiments, the core 1510 and upper flange 1300 may comprise a single component, with a lower flange 1200 comprising a separate component, or the core 1510 and lower flange 1200 may comprise a single component with the upper flange 1300 comprising a separate component.

Figure 3:
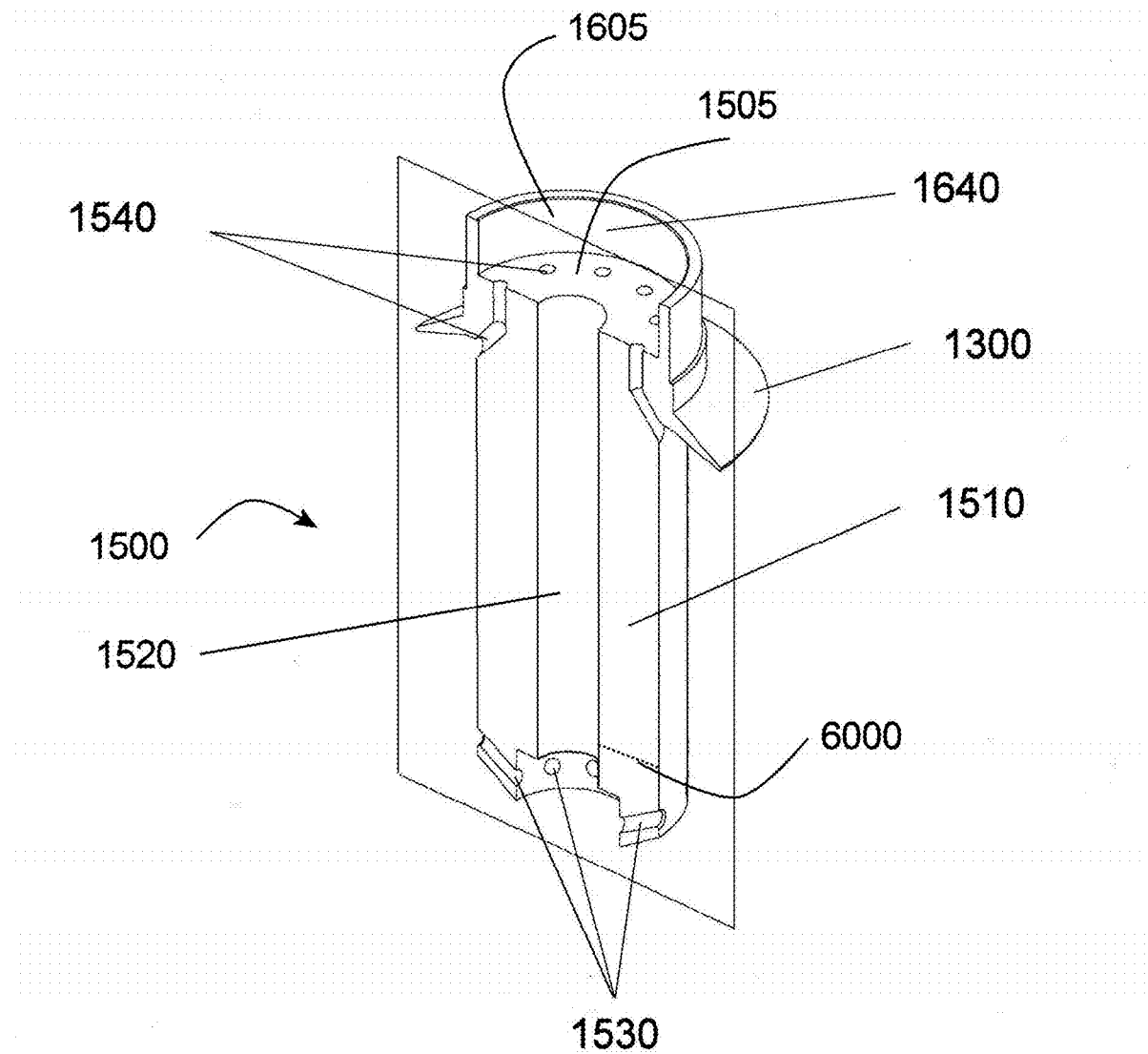
FIG. 3 is an isometric cutaway view of the core and upper flanges of the single use component of the embodiment the centrifuge system of FIG. 1.

An embodiment of a unitary core 1510 and upper flange 1300 is illustrated in FIG. 3. This unitary component would be joined to lower flange 1200 to create the internal supporting structure 1500 of the single use components of centrifuge 1000. This structure anchors the flexible liner 1100 around a fixed internal rigid or semi-rigid support structure 1500 at both the top and bottom. When the centrifuge system is in use, the flexible liner 1100 is also supported externally by the walls and cover of the multiple use structure 3000.

Figure 12:
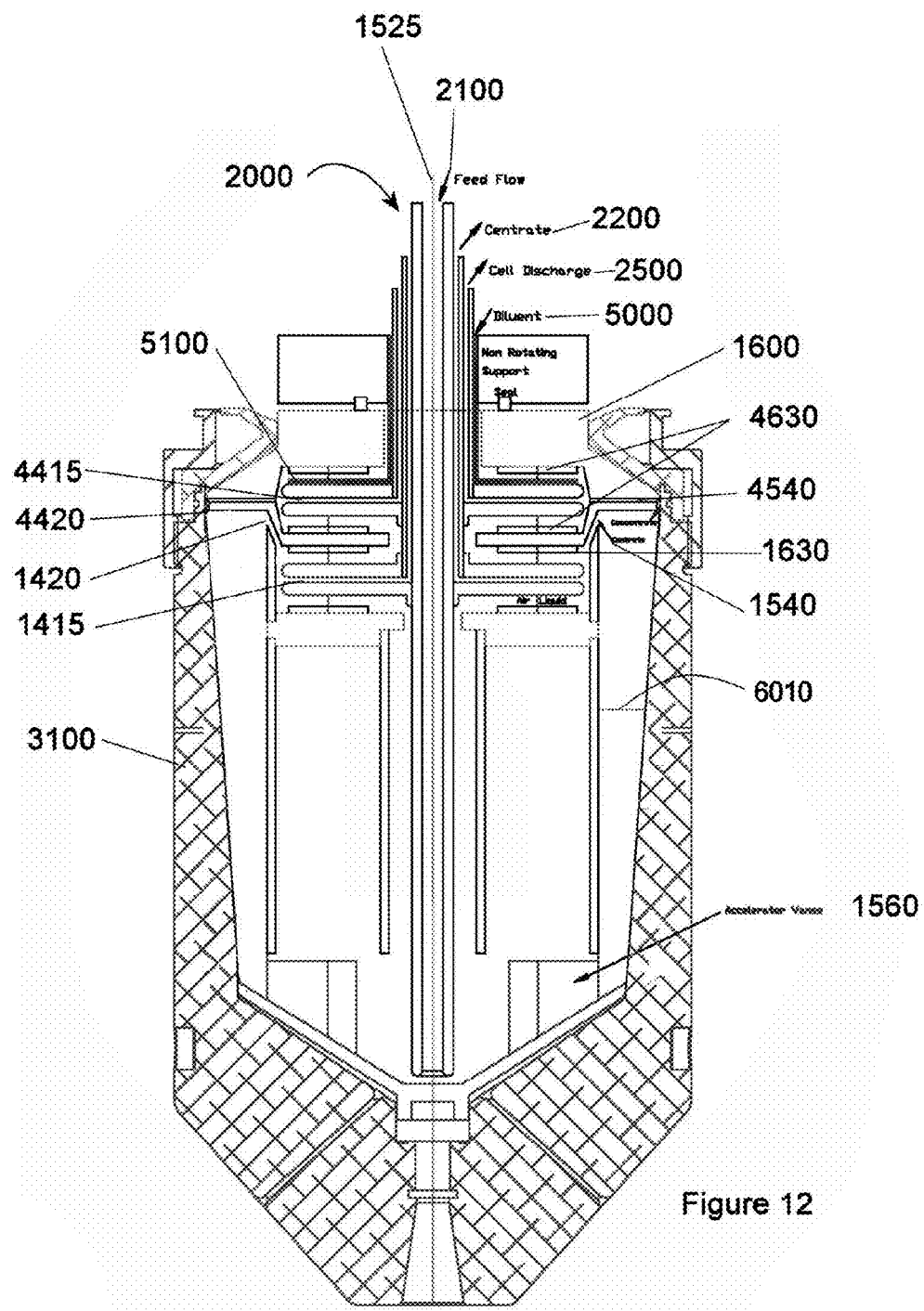
FIG. 12 is a schematic view of a continuous concentrate discharge centrifuge system with diluent injection.

The separation chamber 1550 is an open chamber which is roughly cylindrical in shape, bounded roughly by the exterior surface 1515 of the core 1510 and the flexible liner 1100, and by the upper surface 1210 of the lower flanges 1200 and the lower surface 1310 of the upper flanges 1300. The separation chamber 1550 is in fluid connection with the feed tube 2100 via holes 1530 extending from the central cavity 1520 of the core 1510 to the exterior surface 1515 of the core 1510. The separation chamber 1550 is also in fluid connection with the pump chamber 1420 via similar holes 1540 through the core structure 1500. In this example, holes 1540 angle upward, toward the pump chamber 1420, opening into the separation chamber 1550 just below the junction between the core 1510 and upper flanges 1300. As can be seen in FIG. 12, holes 1420 or 4420 may enter pump chambers at an angle other than upward, including horizontally or at a downward angle. In addition, in some embodiments holes 1420, 4420 may be replaced by slits, or gaps between accelerator fins.

FIG. 1 also shows a feed/discharge assembly 2000 which includes a feed tube carrier 2300, through which feed tube 2100 extends into the position shown in FIG. 3, close to the bottom of centrifuge structure 1000. In this position the feed tube 2100 can perform both feed and discharge functions without being moved. Shearing forces during the feeding process may be minimized by careful design of the gap between the nozzle 2110 of the feed tube 2100 and the upper surface 1210 of the lower flanges 1200, the diameter of the nozzle 2110 of the feed tube 2100, and the angular velocity of the centrifuge. U.S. Pat. No. 6,616,590, the disclosures of which are fully incorporated herein by reference, describes how to select appropriate relationships to minimize the shearing forces. Other suitable feed tube designs which minimize the shearing forces associated with feeding a liquid cell culture into a rotating centrifuge which are known to those skilled in the art may also be used.

FIG. 1 further includes a centripetal pump 1400 for discharging centrate through a centrate discharge path 2200. In the embodiment shown in FIG. 1, the centrate pump 1400 is located above the upper flange 1300 in a pump chamber 1420. Pump chamber 1420 is a chamber defined by the upper surface 1505 of the core 1510 and the inner surfaces 1605, 1620 of a centrifuge cover 1600. The centrifuge cover 1600 may include cylindrical walls 1640 and a mating cap portion 1610 shaped like a generally circular disk (shown in FIG. 5). The centrifuge cover 1600 may be formed as a unitary body, or from separate components.

As discussed in more detail below, in other embodiments, the shape and position of the centrate pump chamber 1420 may vary. Chamber 1420 will generally be an axially symmetric chamber near the upper end of the core structure 1500 which is in fluid connection with the separation chamber 1550 via holes or slits 1530 which extend from adjacent the exterior of the core 1515 into the centrate pump chamber 1420. In some embodiments, as may be seen most clearly in FIGS. 11 and 12, centrate pump chamber 1420 may be located in a recess within chamber 1550.

Centrate pump 1400 comprises a pair of paring disks 1410. Paring disks 1410 are two thin circular disks (plates), which are axially aligned with the axis 1525 of core structure 1500. In the embodiment illustrated in FIGS. 1-5, paring disks 1410 are held stationary relative to the centrifuge structure 1000, and are separated from each other by a fixed gap 1415 (labeled in FIG. 10). The gap 1415 between the paring disks 1410 forms part of a fluid connection for removing centrate from the centrifuge 1000, which permits centrate to flow between the paring disks 1410 into a hollow cylindrical centrate discharge path 2200 surrounding the feed tube carrier 2300, terminating in centrate outlet 2400.

The single use centrifuge structure 1000 is contained within a multiple use centrifuge structure 3000. The structure 3000 comprises a bowl 3100 and a cover 3200. The walls of the centrifuge bowl 3100 support the flexible liner 1100 of centrifuge structure 1000 during rotation of the centrifuge 1000. In order to do so, the external structure of the single use structure 1000 and the internal structure of the multiple use structure conform to each other. Similarly, the upper surface of upper flanges 1200, the exterior of an upper portion of core 1510, and a lower portion of the walls 1640 of the centrifuge cover 1600 conform to the inner surface of the multiple use bowl cover 3200, which is also adapted to provide support during rotation. Features of the multiple use bowl 3100 and bowl cover 3200, discussed in more detail below, are designed to ensure that shear forces do not tear the liner 1100 free from the single use centrifuge structure 1000. In some instances, an existing multiple use structure 3000 may be retrofitted for single use processing by selecting a conforming single use structure 1000. In other instances, the multiple use structure 3000 may be specially designed for use with single use structure inserts 1000.

Figure 2:
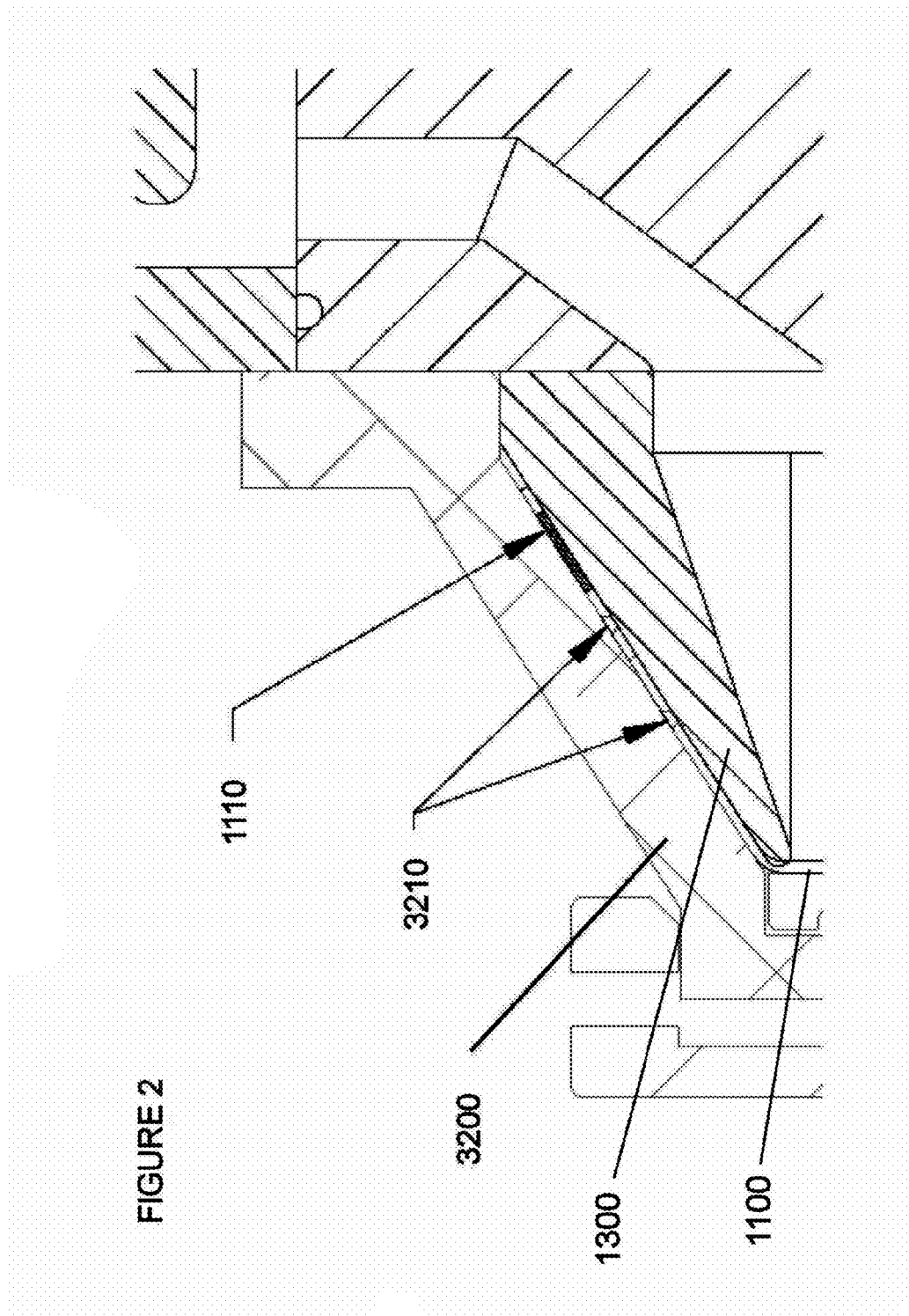
FIG. 2 is a close-up view of the upper flange area of the centrifuge of FIG. 1, which shows a method of sealing the flexible chamber material to the surface of the flange.

FIG. 2 shows a portion of an exemplary structure for upper flanges 1300, plastic liner 1100, and the cover 3200 of a multiple use centrifuge structure 3000 to illustrate sealing the flexible liner 1100 to the upper flanges 1300. The flexible liner 1100 may be a thermoplastic elastomer such as a polyurethane (TPU) or other stretchable, tough, non-tearing, biocompatible polymer, while the upper and lower flanges 1300, 1200 may be fabricated from a rigid polymer such as polyetherimide, polycarbonate, or polysulfone. The flexible liner 1100 is a thin sleeve, or envelope, which extends between and is sealed to the upper and lower flanges 1300, 1200, and forms the outer wall of separation chamber 1550. The composition of the liner 1100 and of the upper and lower flanges 1300, 1200, and core 1510 suggested herein are exemplary only. Those skilled in the art will be able to substitute suitable materials with properties similar to those suggested which are, or may become, known.

A thermal bonding attachment process may be used to bond the dissimilar materials in the area shown in FIG. 2. The thermal bond 1110 is formed by preheating the flange material, placing the elastomeric polymer atop the heated flange, and applying heat and pressure to the elastomeric film liner 1100 at a temperature above the film's softening point. The plastic liner 1100 is bonded to lower flange 1200 in the same manner. Although a thermal bond 1110 is described herein, it is merely exemplary. Other means of creating a similarly strong relatively permanent bond between the flexible film and the flange material may be substituted, such as by temperature, chemical, adhesive, or other bonding means.

The single-use components are pre-sterilized. During the removal of these components from their protective packaging and installation into a centrifuge, the thermal bonds 1110 maintain sterility within the single-use chamber. The stretchable flexible liner 1100 conforms to the walls of reusable bowl 3100 when in use. Reusable bowl 3100 provides sufficient support, and the flexible liner 1100 is sufficiently elastic, to permit the single use structure 1000 to withstand the increased rotational forces which are generated when the larger radius centrifuge 1000 is filled with a liquid cell culture and is rotated with a sufficient angular velocity to reach a settling velocity that permits processing at a rate of about 2-40 liters a minute.

In addition to the thermal bond 1110, sealing ridges or "nubbins" 3210 may be present on bowl cover 3200 to compress the thermoplastic elastomeric film against the rigid upper flanges 1300, forming an additional seal. The same compression seals may also be used at the bottom of the bowl 3100 to seal the thermoplastic elastomeric film against the rigid lower flanges 1200. These compression seals support the thermal bonded areas 1110, by isolating them from shearing forces created by the hydrostatic pressure that develops during centrifugation when the chamber is filled with liquid. The combination of the thermal bond 1110 and the compression nubbin 3210 seals has been tested at 3000×g, which corresponds to a hydrostatic pressure of 97 psi at the bowl wall. The lining should be sufficiently thick and compressible to permit the nubbins 3210 to compress and grip the flexible liner 1100 yet minimize the risk of tearing near the thermal bond 1110 or compression nubbins 3210. In one embodiment, a flexible TPU liner 0.010 inch thick sealed without tearing or leaking.

An embodiment corresponding to the illustrations of FIGS. 1-2 has been tested within a bowl that was 5.5 inches in diameter. At 2000×g it had a hydraulic capacity >7 liters/min and successfully separated mammalian cells to 99% efficiency at a rate of 3 liter/min.

Figure 10:
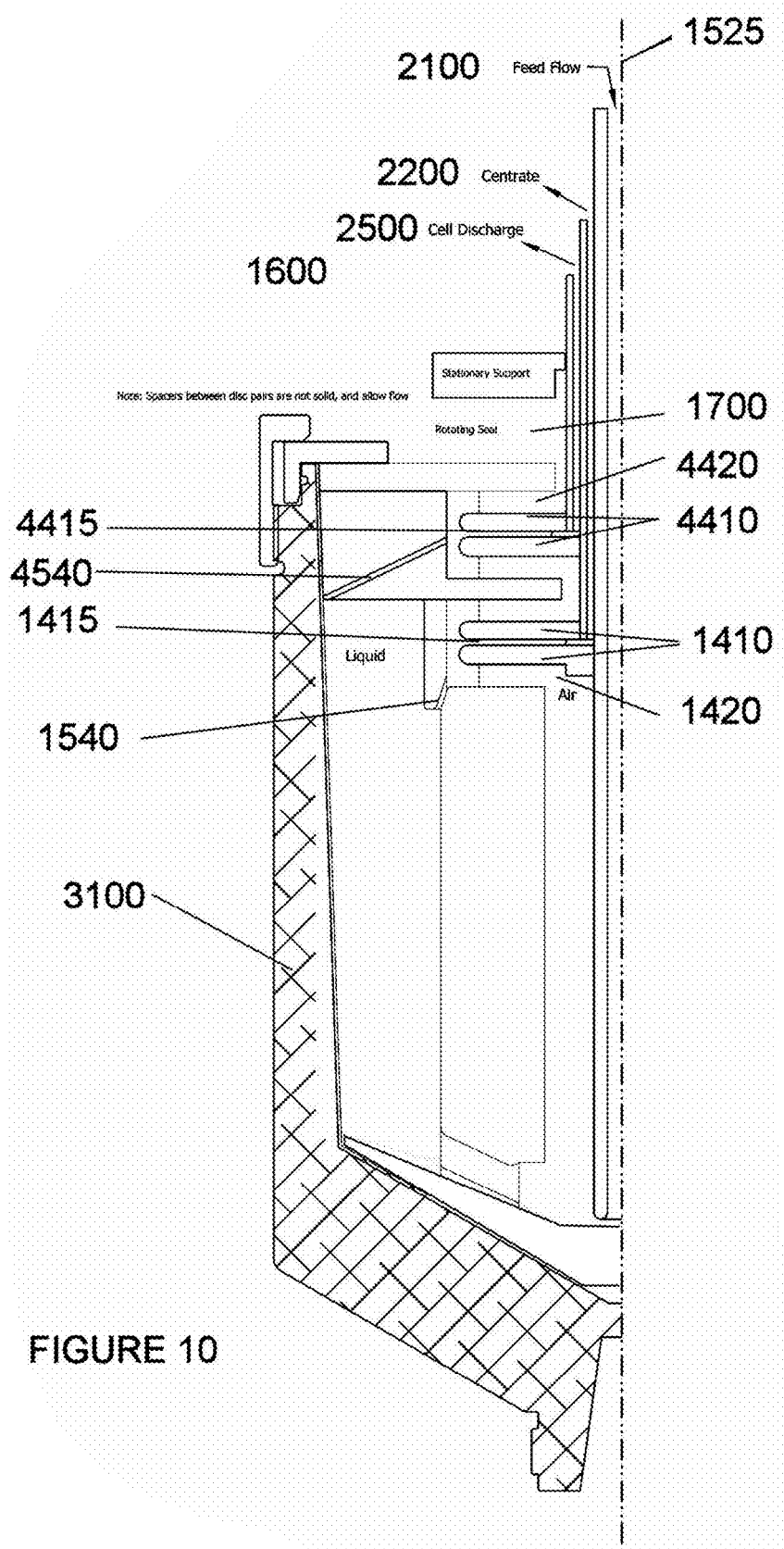
FIG. 10 is a schematic view of a portion of a continuous concentrate discharge centrifuge system.
Figure 11:
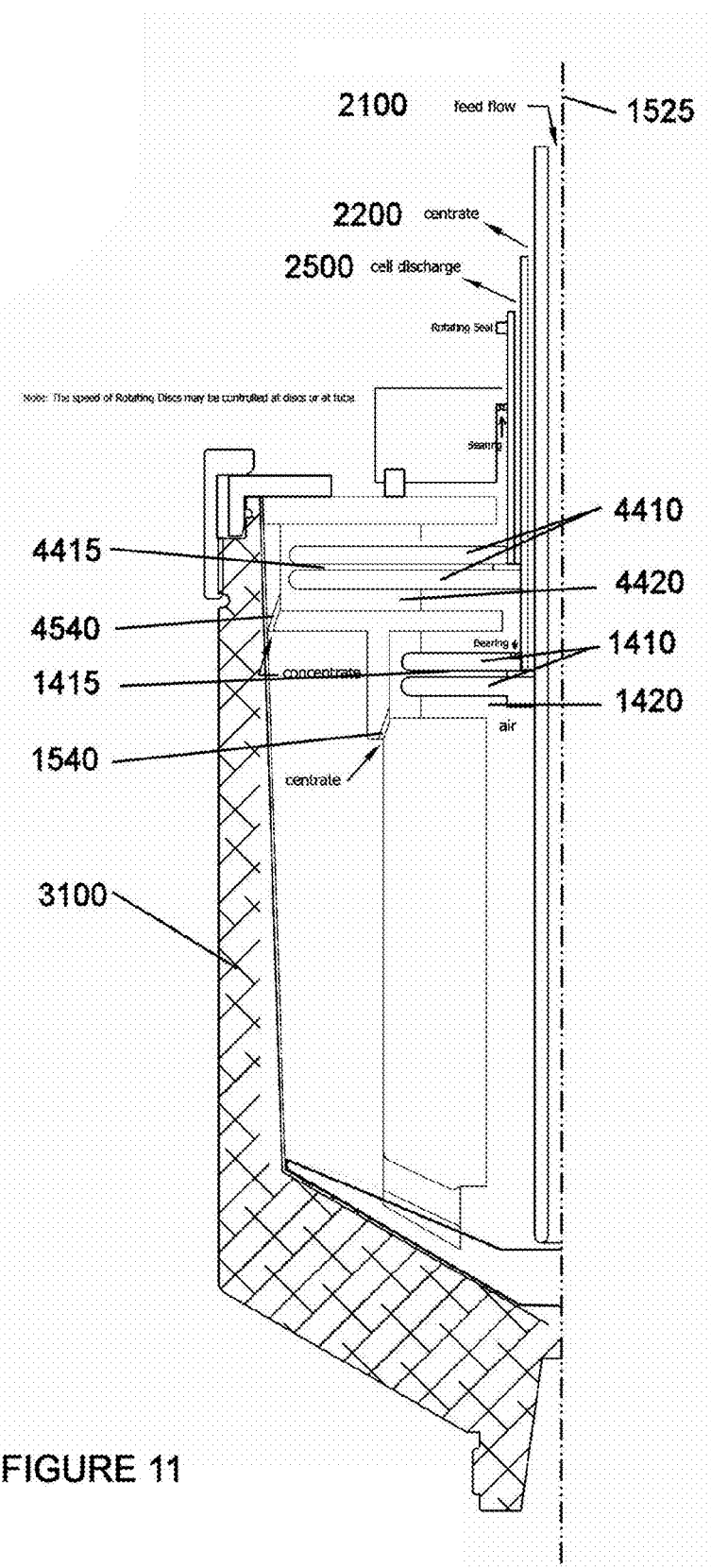
FIG. 11 is a schematic view of a portion of a second embodiment of a continuous concentrate discharge centrifuge system.

In most instances, the upper and lower flanges 1300, 1200 have a shape similar to that illustrated FIG. 1, but in some instances the upper surface of the single use centrifuge structure may have a different shape, as is illustrated in FIGS. 10 and 11. In the embodiments illustrated in FIGS. 10 and 11, rather than having a generally conical bowl cover 3200, to conform to generally conical upper flanges 1300, both the upper flanges and the bowl cover are relatively disk shaped. Those skilled in the art will be able to adapt the sealing techniques described herein for use with differently shaped sealing surfaces.

Figure 4:
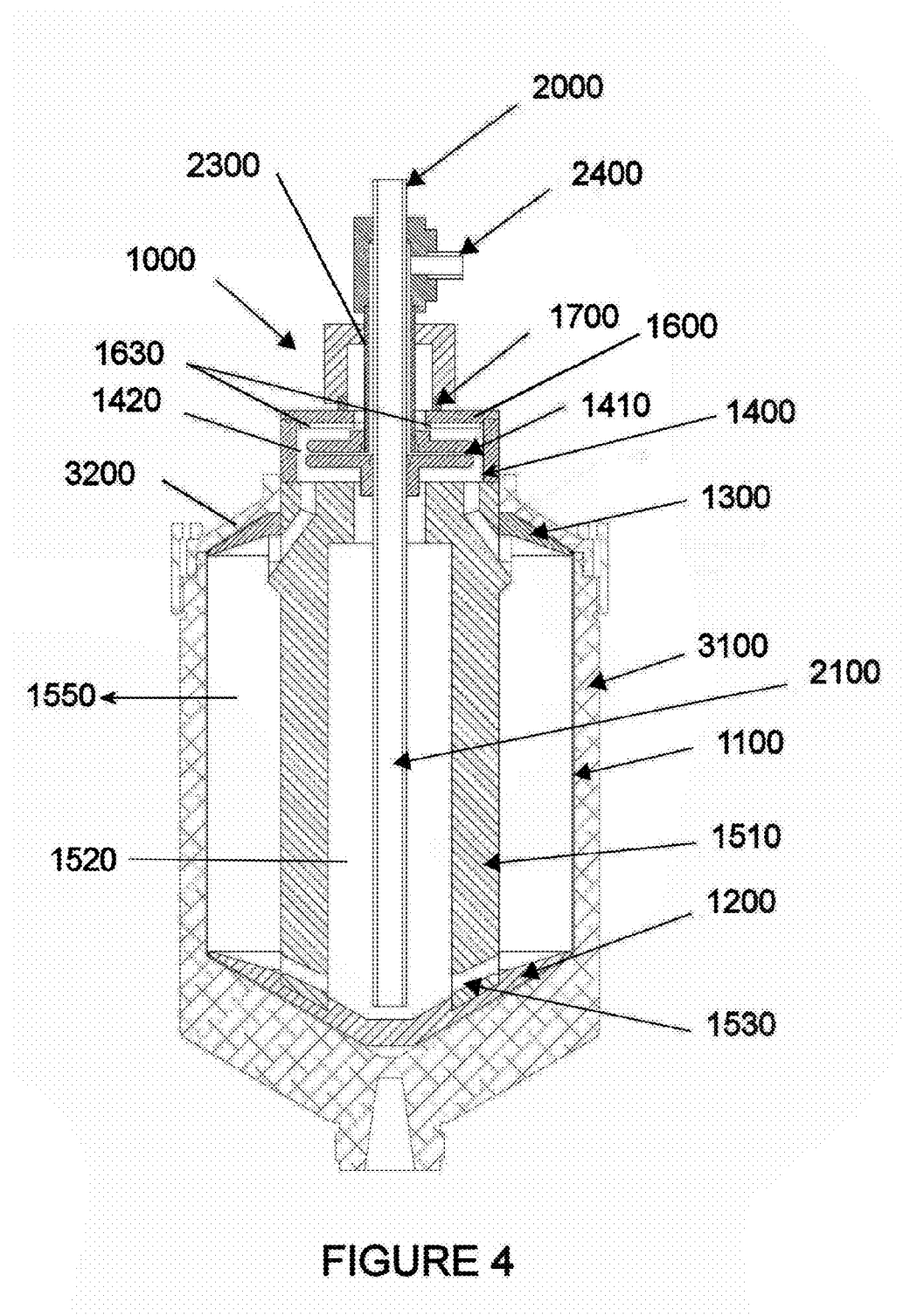
FIG. 4 is a schematic view of the embodiment illustrated in FIG. 1, in which the pump chamber of the centrifuge system includes accelerator fins.
Figure 5:
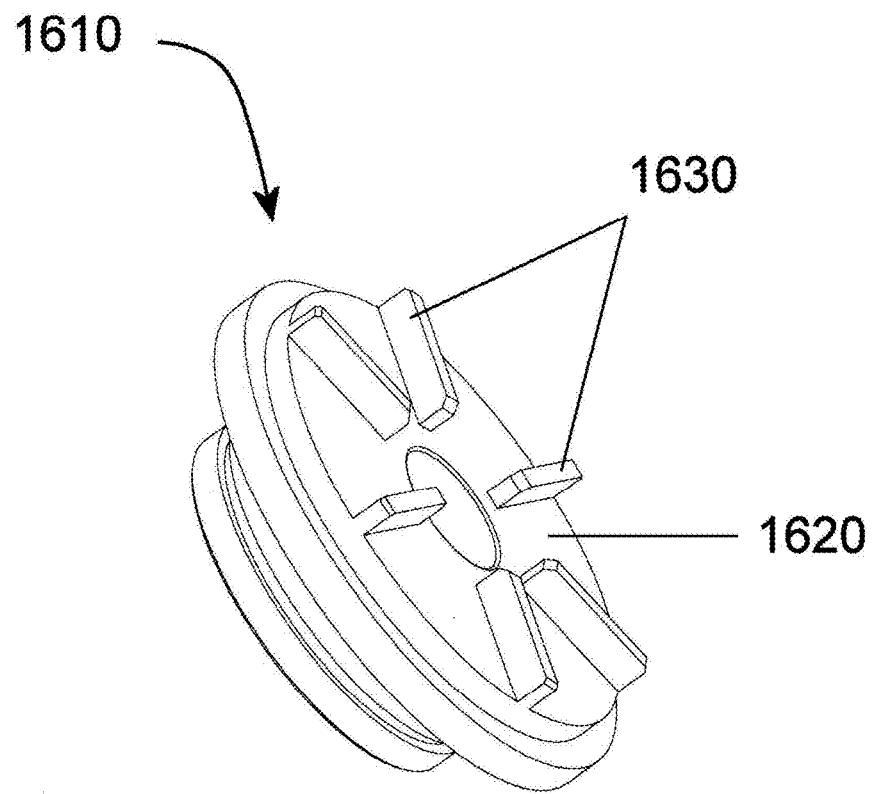
FIG. 5 is an isometric view of the top of the pump chamber of the embodiment of the centrifuge system illustrated in FIG. 4.

FIGS. 4-5 illustrate an embodiment with features to improve the efficiency of the centripetal pump 1400. As shown in detail in FIG. 5, this embodiment of an internal structure for single use components similar to that illustrated in FIGS. 1 and 2 includes a plurality of radial fins 1630 on the inner face 1620 of a cap portion 1610 of the pump chamber 1420. FIG. 5 shows the inner face 1620 of the cap portion 1610 of centrifuge cover 1600. The radial fins 1630, may be thin, generally rectangular, radial plates, extending perpendicularly from the inner surface 1620 of the cap portion 1610. In the exemplary embodiment, six (6) fins 1630 are illustrated, but other embodiments may include fewer or more fins 1630. In this embodiment, fins 1630 form part of the inner face of cap 1620, but in other embodiments may comprise the upper surface 1620 of pump chamber 1420, which may take a form other than cap 1610. When the centrifuge system 10000 is in use, fins 1630 are located above the paring disks 1410 of the centripetal pump 1400 in the chamber 1420. These fins 1630 transmit the angular rotation of the centrifuge 1000 to the centrate within in the pump chamber 1420.

This increases the efficiency of the centripetal pump 1400, stabilizing the gas to liquid interface in the pump chamber 1420 above the paring disks 1410, and increasing the size of the gas barrier. The gas barrier is a generally cylindrical column of gas extending from the exterior of the feed/discharge mechanism 2000 outward into the pump chamber 1420 to the inner surface of the rotating centrate. This increase in the size of the barrier occurs because the resulting increase in angular velocity of the centrate forces the centrate toward the wall of the centrifuge. When rotating centrate within the pump chamber 1420 comes into contact with the stationary paring disks 1410 the resulting friction may decrease the efficiency of the pump 1400. The addition of a plurality of radial fins 1630, which rotate with the same angular velocity as the centrate, overcomes any reduction in velocity that might otherwise result from the encounter between the rotating centrate and the stationary paring disks 1410.

Figure 6:
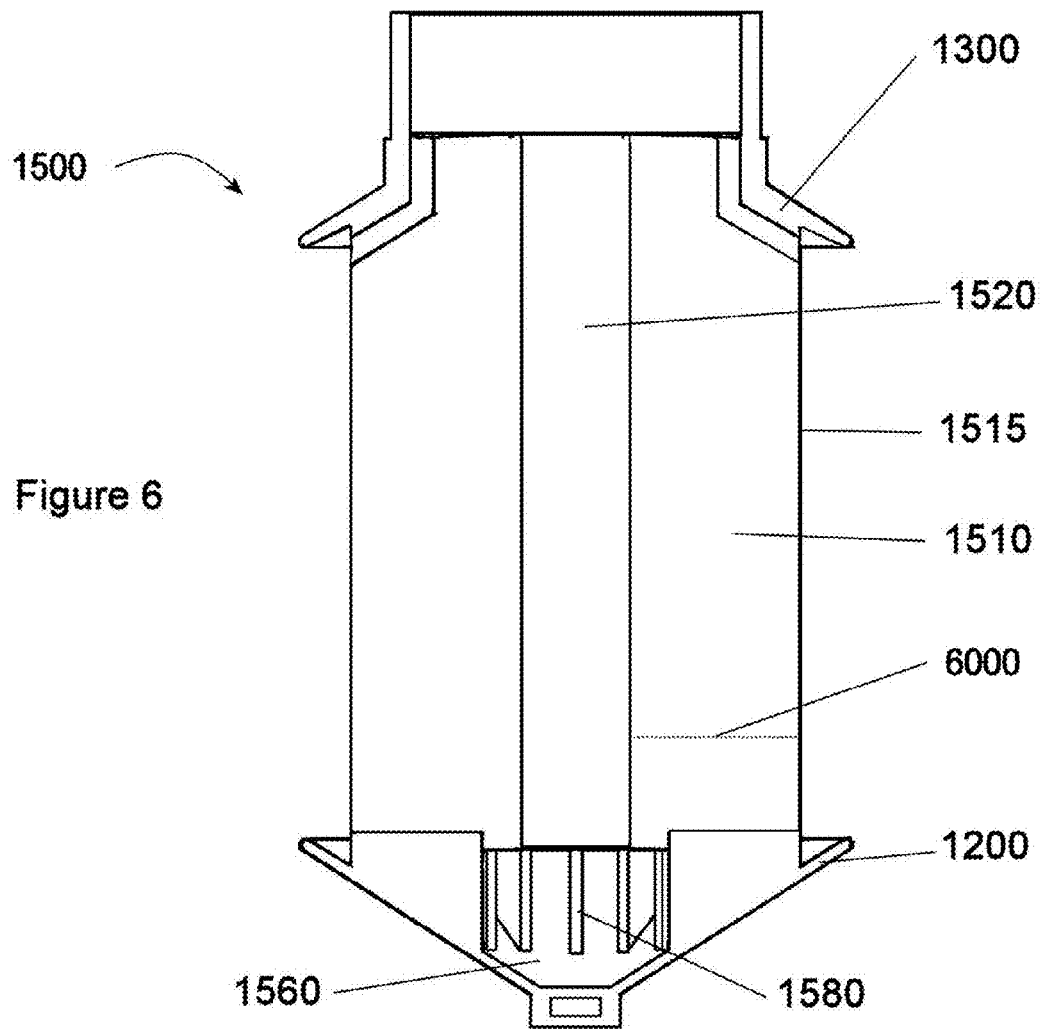
FIG. 6 is an isometric cutaway view of the core, upper flanges, lower flanges, of a single use centrifuge system with an enlarged core diameter (to create a shallow pool centrifuge), and a feed accelerator.

FIG. 6 shows an exemplary embodiment of an improved core structure 1500 for use in high turbidity feeds. Core structure 1500 includes a core 1510, upper flange 1300, and lower flange 1200. Core 1510 has a cylindrical central cavity 1520 adapted to permit feed tube 2100 to be inserted into the central cavity 1520. The distance from the central axis 1525 to the exterior of core 1515 (the core width, represented by dashed line 6000 in FIG. 6) is larger than the corresponding distance in the embodiment illustrated in FIG. 3. The larger diameter core 1510 decreases the depth (represented by dashed line 6010) of the separation chamber 1550, making centrifuge 1000 operate as a shallow pool centrifuge. The depth 6010 of a separation chamber 1550 is generally the distance between the exterior of the core 1510 and the flexible liner 1100, labeled in FIGS. 1 and 12. A shallow pool centrifuge is one which has a depth 6010 which is small, relative to the diameter of the centrifuge. As can be seen in the exemplary embodiment illustrated in FIG. 12, in order to facilitate removal of the cell concentrate, the shallow pool depth 6010 may vary from shallower at the bottom of separation chamber 1550 to somewhat deeper the top of the separation chamber 1550. In the embodiments illustrated herein, the ratio of the average separation pool depth 6010 to the core width is 1:1 or lower. An example of a shallow pool centrifuge is offered as an optional model of the ViaFuge centrifuge system, manufactured by Pneumatic Scale Corporation. The advantage of a shallow pool centrifuge is that it enables separation at higher feed flow rates. This is accomplished by virtue of a higher average g-force for a given inner bowl diameter, which creates a higher sedimentation velocity at a given angular velocity. The resulting enhanced separation performance is beneficial when separating highly turbid feeds containing a high concentration of cell debris.

The embodiment of the core structure 1500 which is illustrated in FIG. 6 also includes accelerator vanes 1560 as part of the lower flange 1200. Accelerator vanes 1560 (as may be seen in FIG. 12), rather than holes 1530 through a solid core 1510 (as may be seen in FIG. 10-11), comprise an alternate embodiment of a fluid connection between the central cavity 1520 of the core 1510 and the separation chamber 1550.

Figure 7:
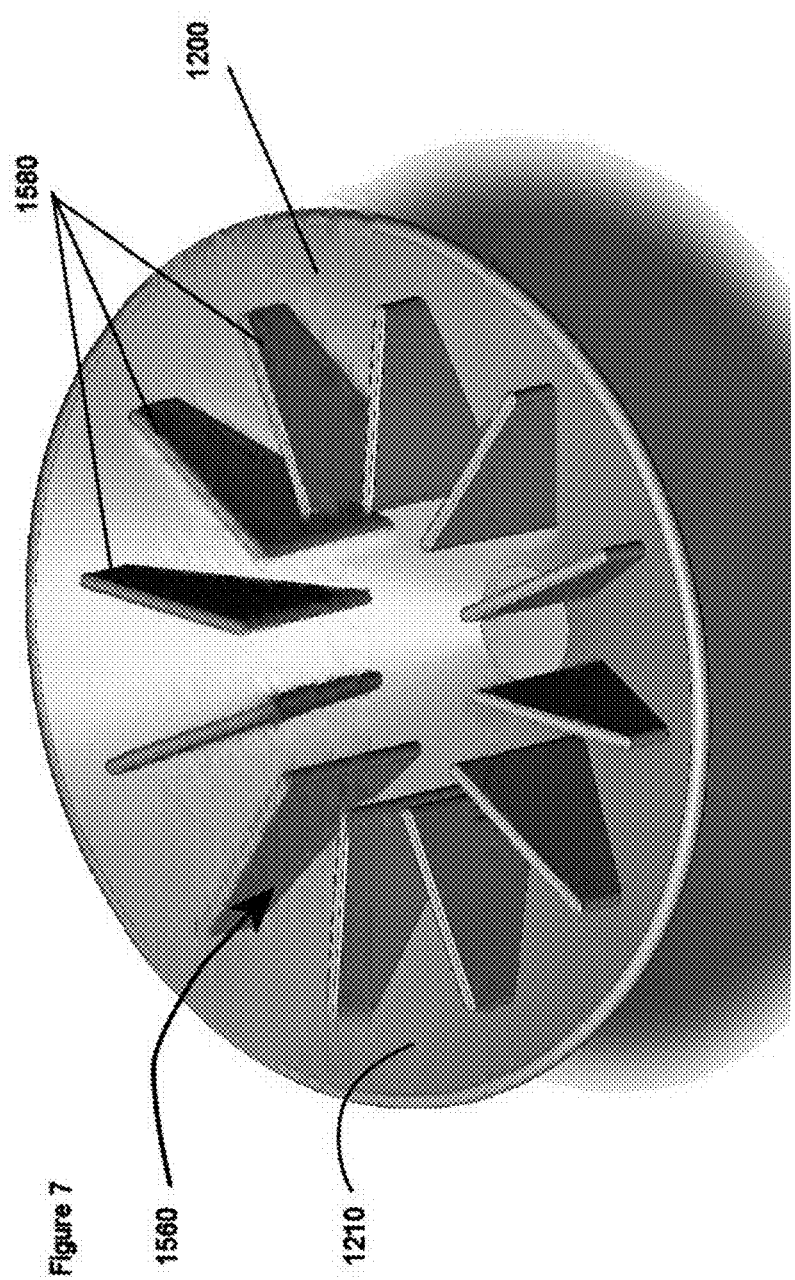
FIG. 7 is an isometric view of the feed accelerator of FIG. 6.
Figure 8:
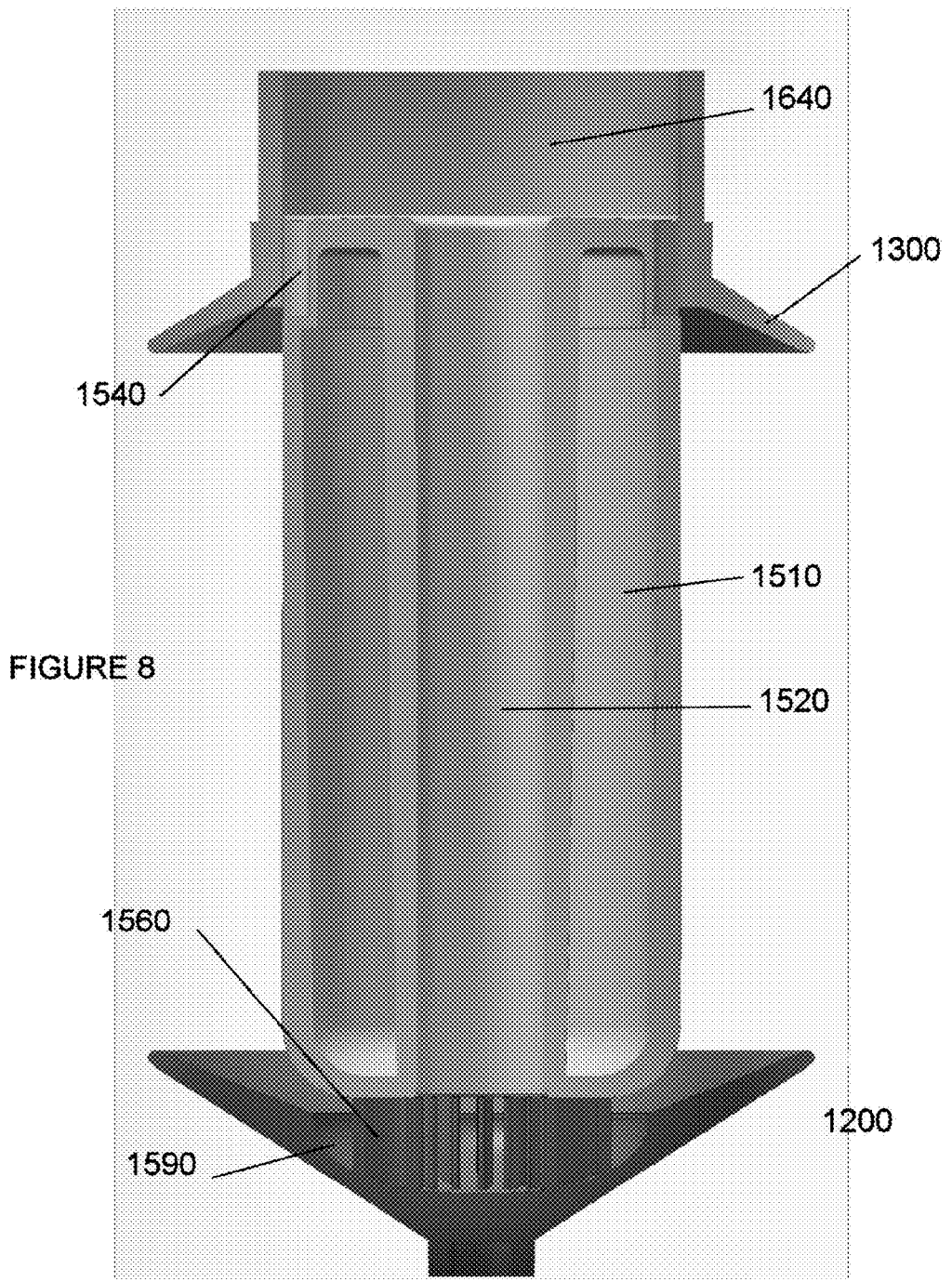
FIG. 8 is an isometric cutaway view of the core and upper flanges of a single use centrifuge system with a standard core diameter, and a feed accelerator with curved vanes and an elliptical bowl.
Figure 9:
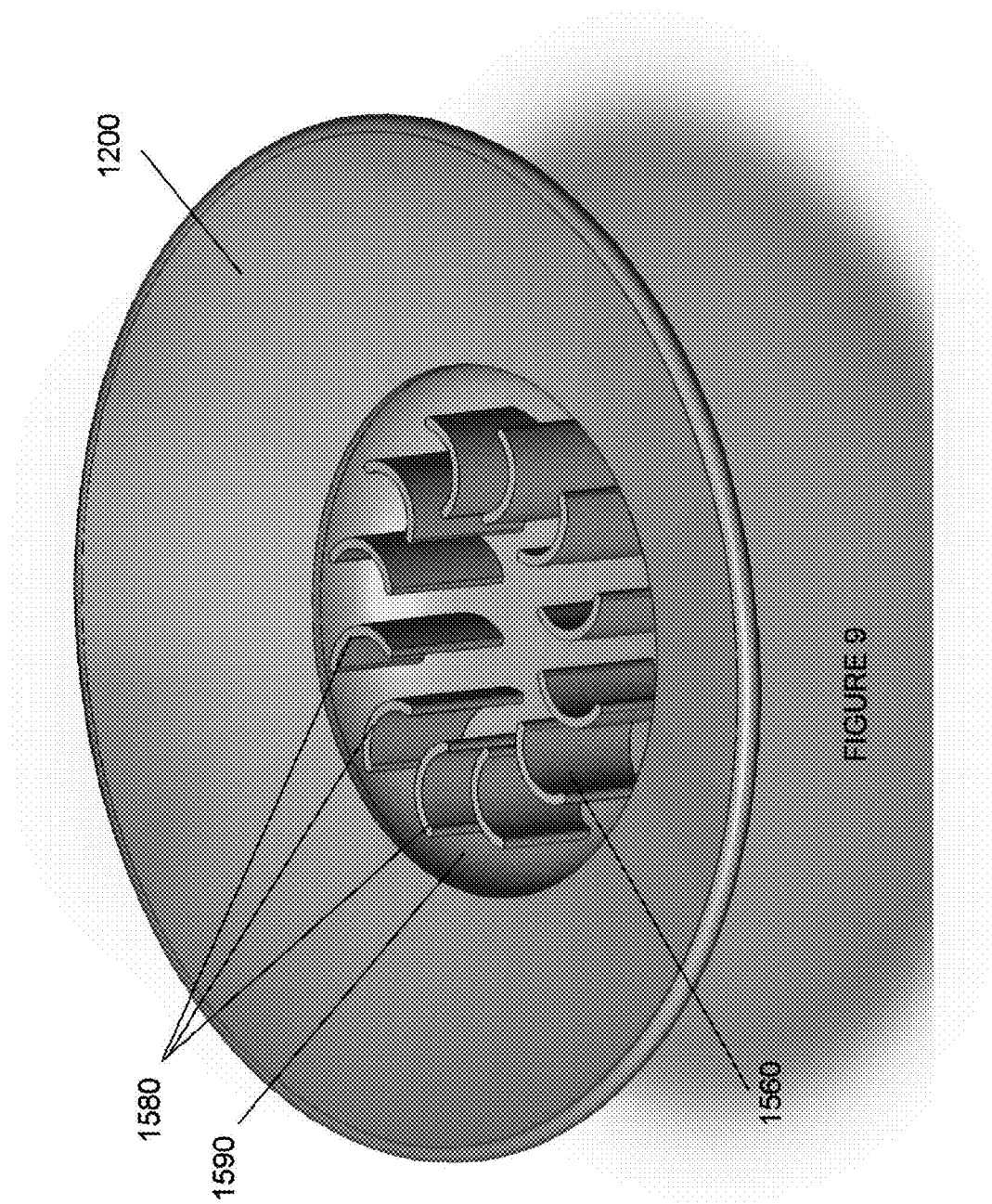
FIG. 9 is an isometric view of the feed accelerator of FIG. 8.

In the exemplary embodiment of a core structure 1500 shown in FIG. 6, accelerator vanes 1560 comprise a plurality of radially, generally rectangular, spaced thin plates 1580 extending upward from the upper conical surface of the lower flange 1200. Plates 1580 extend upward orthogonal to the base of the core 1510. Plates 1580 generally extend radially outward from near the axis 1525 of the core 1510. In the exemplary embodiment, there are 12 plates 1580, as may be seen most clearly in FIG. 7. In other embodiments there may be fewer or more than 12 plates 1580. In addition, in other embodiments the plates 1580 may be curved in the direction of rotation of the centrifuge 1000, as shown in an exemplary embodiment in FIG. 9. The interior surface of lower flange 1200 may be modified to form an elliptical accelerator bowl 1590, with the curved plates extending upward therefrom. These embodiments are intended to be exemplary, and those skilled in the art may combine them in different ways or may, within the scope of the invention, modify these embodiments to further benefit from the turbidity reduction these plates and the shape of the lower flange 1200 and/or an embedded accelerator bowl create.

Further features of an embodiment of a single use centrifuge 1000 which is designed to operate continuously or semi-continuously are illustrated in FIGS. 10-12. The exemplary embodiment illustrated in FIG. 10 includes a second centripetal pump 4400 for removal of cell concentrate. Centripetal pump 4400 for the removal of cell concentrate is located above the centripetal pump 1400 for removal of centrate. Centripetal pump 4400 includes a pump chamber 4420 and paring disks 4410. A plurality of holes or a continuous slits 4540 extend from the upper outer circumference of the separation chamber 1550 into pump chamber 4420, providing fluid connection from outer portion of the separation chamber 1550 to the second pump chamber 4420. As with pump chamber 1400, pump chamber 4400 may have a different shape than that illustrated in FIGS. 10-12, but will generally be an axially symmetric chamber near the upper end of the core structure 1500 which is in fluid connection with the separation chamber 1550. As with pump chamber 1400, pump chamber may be partially or entirely recessed within core structure 1500. If a centrate pump chamber 1400 is present near the upper end of the core structure 1500, the cell concentrate pump chamber 4400 will generally be located above it. A pump chamber 4400, for the removal of cell concentrate, will be in fluid connection with separation chamber 1550 via holes or slits 4540 which extend from adjacent the outer upper wall of separation chamber 1550, in order to collect the heavier cell concentrate which is urged there by centrifugal forces.

In the embodiment illustrated in FIG. 10, the paring disks 4410 used in the concentrate discharge pump 4400 are approximately the same radius as those used in the centrate discharge pump 1400, and are rotationally fixed. In other embodiments, such as the one shown in FIG. 11, the paring disks 4410 in the concentrate discharge pump 4400 may have a larger radius than those in the centrate discharge pump 1400, with a correspondingly larger pump chamber 4420. Paring disks of various intermediate diameters may be used as well. The optimum diameter will depend on the properties of the cell concentrate that is to be discharged. Larger diameter paring disks have a higher pumping capacity, but create greater shear.

In the embodiments illustrated in FIGS. 1, 4, and 10, the paring disks 4410 in the concentrate discharge pump 4400 are rotationally fixed. In other embodiments, such as the one shown in FIG. 11, paring disks in 4410 may be adapted to rotate with an angular velocity between zero and the angular velocity of the centrifuge 1000. The desired angular velocity can be controlled by a number of mechanisms that are known to those skilled in the art. An example of a means of control is an external slip clutch that allows the paring disks 4410 to rotate at an angular velocity that is a fraction of that of the centrifuge 1000. Other means of controlling the angular velocity of the paring disks will be apparent to those skilled in the art.

In the embodiments illustrated in FIGS. 1, 4, 10-12, the gaps 1415, 4415 between paring disks 1410 and 4410 are fixed. In other embodiments, such as the embodiment in FIG. 13, the gaps 1415, 4415 between paring disks 1410 and 4410 may be adjustable, in order to control the flow rate at which centrate or concentrate are removed from the centrifuge 1000. One of each pair of paring disks 1410 and 4410 is attached to a vertically moveable throttle tube 6100. Throttle tube 6100 may be moved up or down in order to narrow or widen the gap 1415, 4415 between each pair of the paring disks 1410, 4410. In addition, an external peristaltic pump 2510 (not shown) may be added to the concentrate removal line 2500 (not shown) to aid in removal of concentrate. This pump 2510 may be controlled by a sensor 4430 in the pump chamber 4420. The sensor 4430 (not shown) may also be used to control a diluent pump 5150 in order to synchronize concentrate removal with the addition of diluents.

Figure 13:
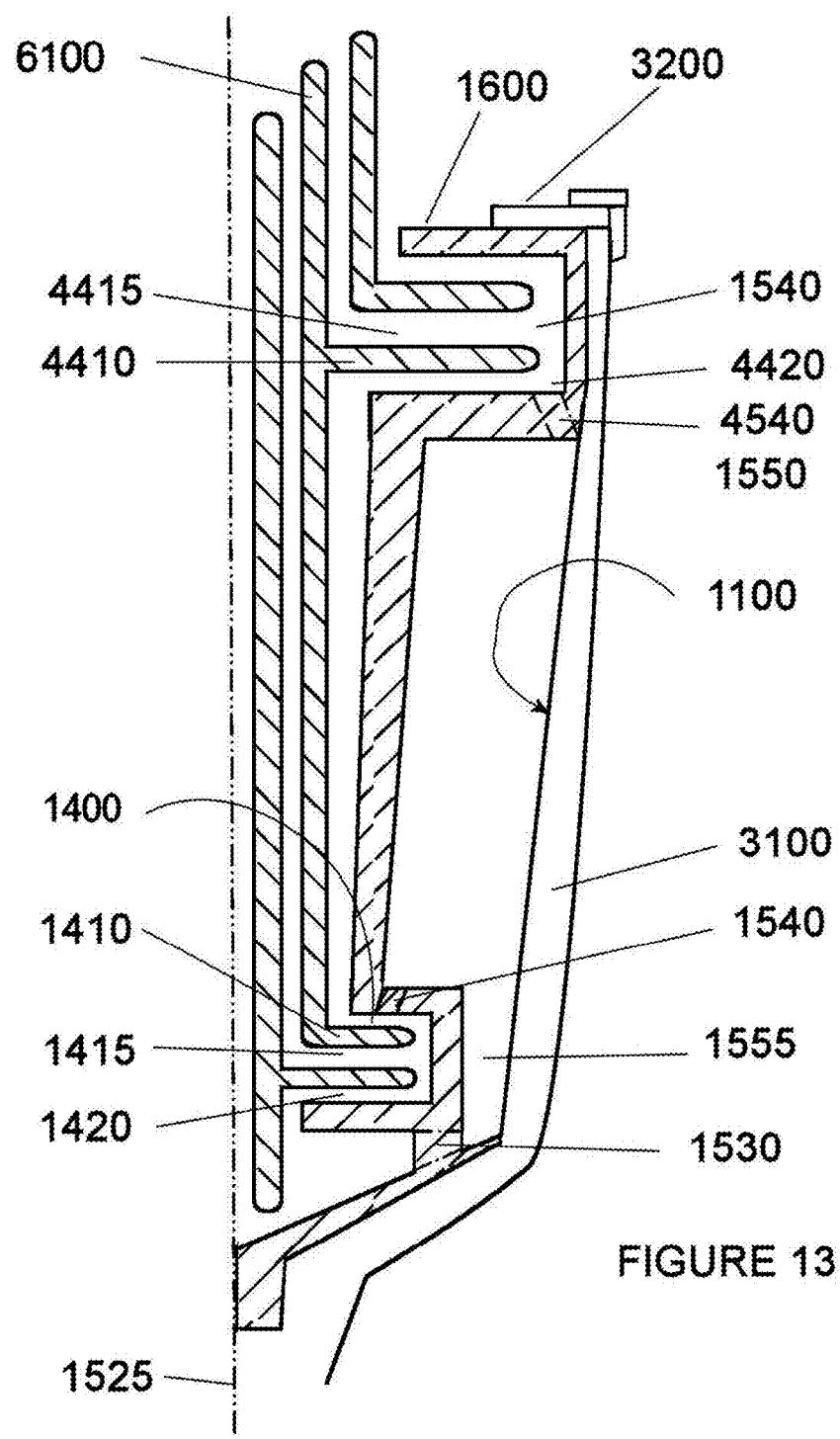
FIG. 13 is schematic view of a portion of a third embodiment of a continuous concentrate discharge system, with a throttle mechanism for the centripetal pumps.
Figure 14:
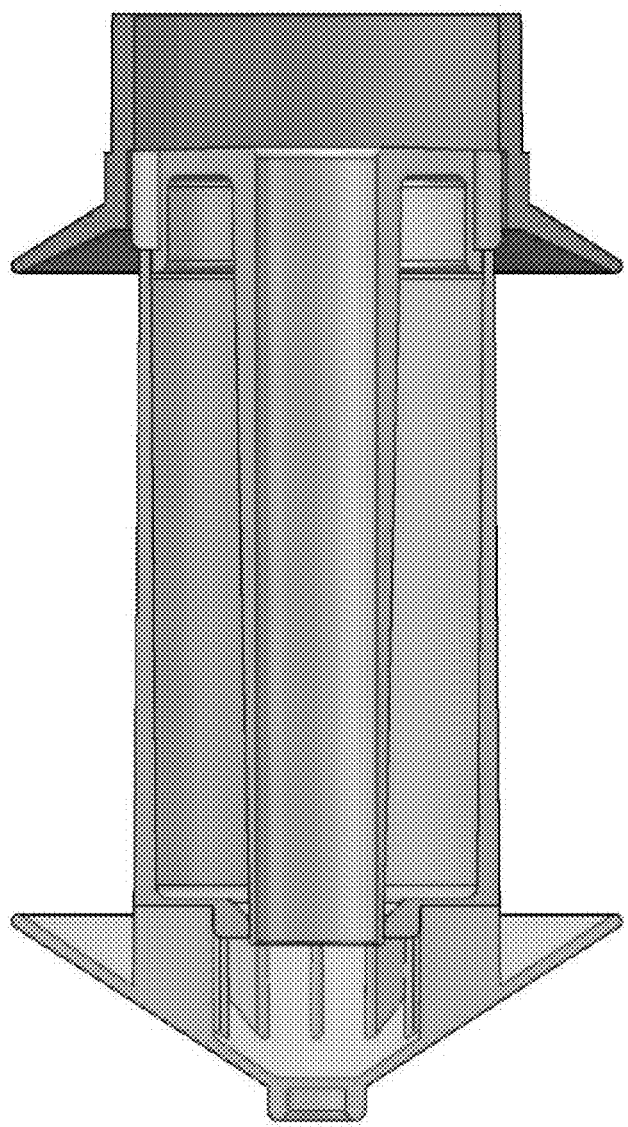
FIG. 14 is an isometric cutaway view of the core and upper flanges of a single use centrifuge system with a standard core diameter, and a feed accelerator with straight vanes.
Figure 15:
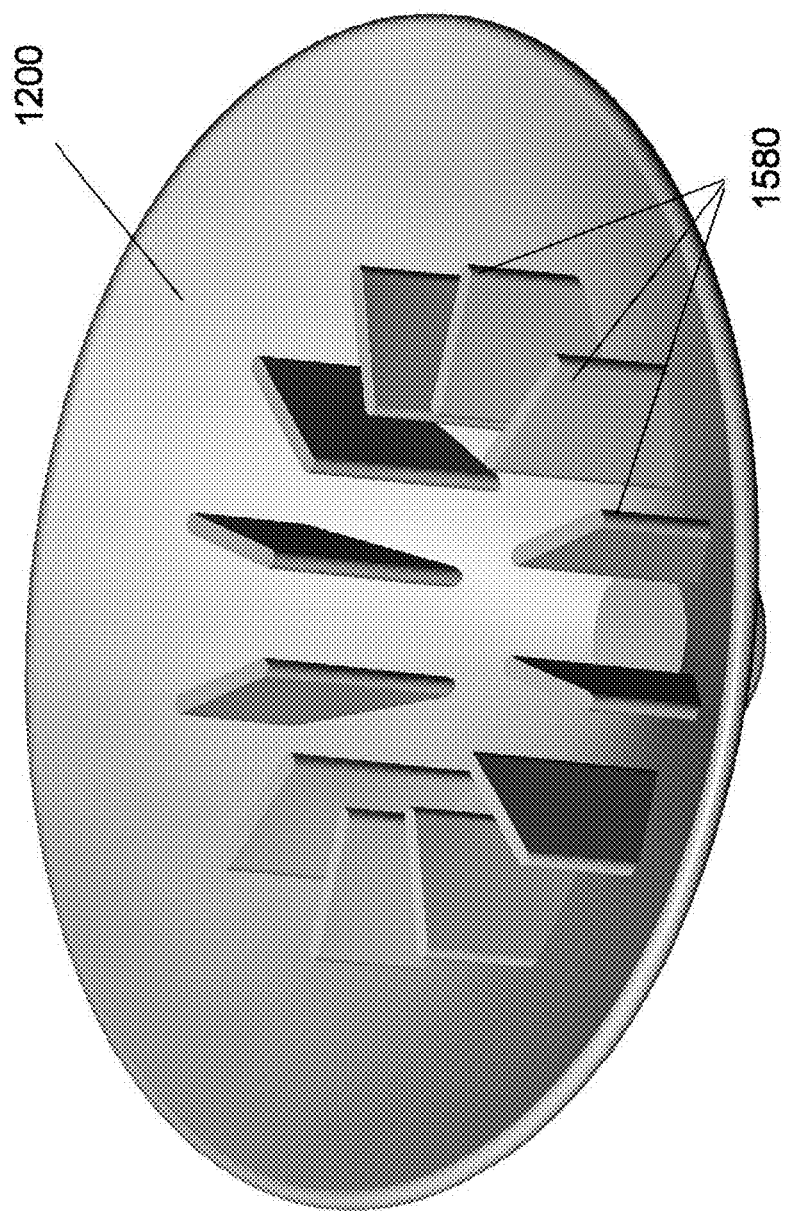
FIG. 15 is an isometric view of the feed accelerator of FIG. 14.

Also illustrated in FIG. 13 is an embodiment in which the centrate pump 1400 is located at the base of the centrifuge 1000. In the embodiment illustrated in FIG. 13, a centrate well 1555 is created between the pump chamber 1420 and the flexible liner 1100. Holes 1530 extend from the core 1510, below the pump chamber 1420, into the centrate well 1555. In addition, in the exemplary embodiment illustrated, holes 1540 extend from the separation chamber 1550, adjacent the exterior surface 1515 of the core 1510, into the pump chamber 1420 to permit the centrate to be removed using centrate pump 1400. Holes 4540 may also extend between the separation chamber 1550, adjacent its outer upper surface, into pump chamber 4420 to permit cell concentrate to flow into pump chamber 4420 to be removed using centripetal pump 4400.

As noted above, in the exemplary embodiment illustrated, the gaps 1415, 4415 between the paring disks 4410 and 1410 may be adjustable by use of a throttle tube 6100 connected to one of each pair of paring disks 4410, 1410. Throttle tube 6100, and the attached one of each paring disk pair 4410, 1410, may be moved up or down to narrow or widen gaps 1415, 4415. In the exemplary embodiment illustrated, the throttle tube 6100 is attached to the lower and upper paring disk of paring disk pairs 4410, 1410, respectively. In other embodiments the attachment may be reversed, may used to throttle a single centripetal pump, or may be used to throttle both in parallel (rather than opposition as illustrated in FIG. 13).

As can be seen in the embodiments illustrated in FIGS. 10-12, the wall of the solid multiple use bowl 3100 is thicker at the base than it is in the upper portion, in order to create an internal truncated cone shape to support single use centrifuge 1000 which has a smaller radius at the lower end than at the upper end. This larger radius at the upper end of the separation chamber 1550 moves the denser cell concentrate toward the upper outer portion of the separation chamber 1550 and into centripetal pump chamber 4420. In the embodiment illustrated, the truncated cone shape is created by a multiple use bowl 3100 with a wall which is thicker at the base than it is in the upper portion. Those skilled in the art will recognize that that a multiple use bowl 3100 having an internal truncated cone shape may also include walls of uniform thickness, and that there may be other variations which create the desired internal shape for the multiple use bowl 3100.

In the embodiments illustrated in FIGS. 10-12, feed mechanism 2000 also includes an additional pathway for the removal of cells, or cell concentrate. In the embodiment illustrated in FIG. 1, the cylindrical pathway 2200 around the feed tube 2100 was used to remove centrate. The embodiments illustrated in FIGS. 10-12 also include, a concentric cylindrical pathway for the removal of cells or cell concentrate, referred to as a cell discharge tube 2500. Cell discharge tube 2500 surrounds the centrate removal pathway 2200. If the centrifuge is designed to be used with a concentrate that is expected to be very viscous, an additional concentric cylindrical fluid pathway 5000 may be added around the feed tube 2100 to permit the diluents to be introduced into the cell concentrate pump chamber 4420 in order to decrease the viscosity of the concentrate. The diluent pathway 5000, in the exemplary embodiment illustrated in FIG. 12, comprises a concentric tube surrounding the cell discharge pathway, and opens at the lower end into a thin disk shaped fluid pathway 5100 above paring disks 4410, discharging near the outer edge of the paring disks 4410 to provide fluid communication with the pump chamber 4420. Injecting the diluent by this means, and in this location, limits the diluent to mixing with, and being discharged with, the concentrate rather than being introduced into the centrate, which may be undesirable in some applications. In alternative embodiments, the diluents may be introduced directly onto the upper surface of the paring disks and allowed to spread radially outward, or onto a separate disk located above the paring disks.

The choice of diluent will depend on the objectives of the separation process and the nature of the cell concentrate that is to be diluted. In some cases a simple isotonic buffer or deionized water can serve as the diluent. In other cases, diluents that are specific to the properties of a cell concentrate may be advantageous. For example, in production scale batch cell culture operated at low cell viability, flocculants are commonly added to the culture as it is being fed to a centrifuge to cause cells and cell debris to flocculate or agglomerate into larger particles, which facilitates their separation by increasing their rate of sedimentation. Since both cells and cell debris carry negative surface charges, the compounds used as flocculants are typically cationic polymers, which carry multiple positive charges, such as polyethyleneimine. By virtue of their multiple positive charges, such flocculants can link negatively charged cells and cells debris into large agglomerates. An undesirable consequence of the use of such flocculants is that they further increase the viscosity of cell concentrates. Therefore, a particularly useful diluent in this application is a deflocculant that will disrupt the bonds that increase the viscosity of the cell concentrate. Examples of deflocculants include high salt buffers such as sodium chloride solutions ranging in concentration from 0.1 M to 1.0 M. Other deflocculants that may be useful in reducing the viscosity of cell concentrate are anionic polymers such as polymers of acrylic acid.

In the case of a cell concentrate wherein cell viability is to be maintained, a diluent can be chosen that is a shear protectant, such as dextran or Pluronic F-68. The use of a shear protectant, in combination with an isotonic buffer, will enhance the survival and viability of cells as they are being discharged from the centrifuge.

The exemplary centrifuge illustrated in FIG. 4 operates as described below. During a feed cycle, a feed suspension flows into the rotating bowl assembly through feed tube 2100. As the feed suspension enters the central cavity 1520 of core 1510 near lower flange 1200, it is urged outward along the upper surface of lower flange 1200 by centrifugal forces, passing into the separation chamber 1550 through holes 1530 in core 1510.

Centrate collects in the separation chamber 1550, a hollow, roughly cylindrical space below the upper flange 1300 surrounding core 1510. The centrate flows upward from its entrance into the separation chamber through holes 1530 until it encounters holes 1540 between the separation chamber 1550 and the pump chamber 1420 in the upper portion of the separation chamber 1550, adjacent the core 1410. Particles of density higher than that of the liquid are moved toward the outer wall of the separation chamber 1550 by sedimentation (particle concentrate), away from holes 1530. When the rotation of the centrifuge 1000 is stopped, the particle concentrate moves downward under the influence of gravity to the nozzle 2110 of the feed tube 2100 for removal via the combined feed/discharge mechanism 2000.

During rotation, the centrate enters the centrate pump chamber 1420 through holes 1540. Within the pump chamber 1420, the rotating centrate encounters stationary paring disks 1410, which convert the kinetic energy of the rotating liquid into pressure which urges the centrate being discharged upward through the centrate discharge path 2200 within the feed/discharge mechanism 2000 and out through the centrate discharge tube 2400.

The efficiency of the centripetal pump 1400 is increased by adding radial fins 1630 on the inner surface 1620 of the cap portion 1610 of the rotating pump 1400. These fins 1630 impart the angular momentum of the rotating assembly to the centrate in the pump chamber 1420, which might otherwise slow because of friction when the rotating centrate encounters the stationary paring disks 1410. The centripetal pump 1400 provides an improved means of centrate discharge, over mechanical seals, because of the gas liquid interface within the pump chamber 1420. The gas within the pump chamber 1420 is isolated from contamination by the external environment by the rotating seal 1700. Because the centrate being discharged between the paring disks 1410 does not come into contact with air, either during the feed or discharge process, it avoids the excessive foaming that often occurs when the discharge process introduces air into the cell culture.

In the centrifuge 1000 embodiment illustrated in FIGS. 4-5, cell concentrate is discharged by periodically stopping bowl rotation and the feed flow and then pumping out the cell concentrate that has been collected along the outer walls of the separation chamber 1550. This process is known as intermittent processing. When the volumetric capacity of the separation chamber 1550 is reached, centrifuge rotation is stopped. The cell concentrate moves downward toward nozzle 2110 of feed tube 2100, where the concentrate is withdrawn by pumping it out through the feed tube 2100. Appropriate valving (not shown) external to the centrifuge 1000 is used to direct the concentrate into a collection vessel (not shown). If the entire bioreactor batch has not yet been completely processed, then bowl rotation and feed flow are resumed, and is followed by additional feed and discharge cycles until the full batch has been processed.

As noted above, when the cell culture is concentrated or contains significant cell debris, the process described above slows down because residence time must be increased to capture small debris particles, which necessitates a slower feed flow rate and the separation chamber 1550 fills rapidly and rotation must be halted frequently and repeatedly for each culture batch. In addition, the cell concentrate tends to be more viscous so gravity does not work as efficiently to drain the cell concentrate to the bottom of the centrifuge 1000 so it takes longer and, in some instances, may require a wash to remove the remaining cells.

The single use centrifuge, as modified in the exemplary embodiments illustrated in FIGS. 6-13, creates a higher average settling velocity without an increase in angular velocity, permits the centrifuge 1000 to run continuously or semi-continuously, and allows a diluent to be added to the cell concentrate during the cell removal process so that the removal of cells is more easily and more completely accomplished.

Embodiments of a single use centrifuge 1000 shown in FIGS. 6-12 operate as discussed herein. Feed suspension enters the single use centrifuge 1000 via feed tube 2100. As the feed suspension encounters accelerator vanes 1560, the vanes 1560 impart an angular velocity to the feed suspension which approaches the angular velocity of the single use centrifuge 1000. The use of vanes 1560, rather than holes 1530, provides for a greater volume of feed suspension to enter the separation chamber 1550 at a slower radial velocity, avoiding the jetting which occurs when the feed suspension is forced through holes 1530 having smaller cross sectional openings than the openings between the vanes 1560. This reduction in velocity of the feed stream as it enters the separation zone, or pool, minimizes disruption of the liquid contents of the pool, which allows for more efficient sedimentation.

As the centrifuge 1000 rotates, the particles which are denser than the centrate are urged toward the outside of the separation chamber 1550, leaving the particle free centrate near the core 1510. The centrifuge bowl 3100 has the shape of an inverted truncated cone, with a wider radius at the upper end than the lower end. The centrifugal force causes the particles to collect in the upper and outer portion of the chamber. The centrifuge 1000 may operate with semi-continuous discharge of concentrate. The centrate discharge works, generally, as described with respect to FIG. 4. The cell concentrate discharge works similarly, with the cell concentrate collecting near the upper outer portion of the separation chamber 1550 and enter the concentrate discharge pump chamber 4400 via holes 4540 adjacent the upper outer wall of the separation chamber 1550.

The rate of feed of suspension, as well as the angular velocity of rotation, may be monitored using a vibration sensor system such as the one described in published PCT Application No. WO 2011/123371, incorporated by reference herein. Such a sensor system permits the centrifuge to be filled at a lower rate until the vibrations indicate the centrifuge is nearly full, then to adjust the feed rate and angular velocity appropriately in response to this information. Typically, the feed rate will be decreased or stopped once the centrifuge is nearly full and the angular velocity will be increased in order to increase the settling velocity and once the settling and discharge is essentially complete, the cycle will be repeated. If the system is optimized using the additional features described herein to diminish the need to interrupt the process, it may be possible to operate the system continuously, or nearly continuously, at the angular velocity needed for settling.

With semi-continuous concentrate discharge, the suspension continues to be fed into the centrifuge 1000, using concentrate pump 4400 operating intermittently to remove concentrate. The operation of concentrate pump 4400 may be controlled by an optical sensor in the concentrate discharge line that indicates the presence or absence of concentrate being discharged. In lieu of a concentrate pump 4400, the discharge cycle may be managed electronically using a controller and sensors which determine when to open and shut a valve for the most efficient processing of the fluid suspension.

The average rate of discharge may further be controlled by using a centrifuge 1000 with an adjustable gap between the paring disks 4410, 1410. It should be noted that it may only be desired or necessary for one set of paring disks 4410, 1410 to be adjustable. The gap between paring disks 4410, 1410 (which forms an essential part of the fluid pathway out of the centrifuge 1000) may be opened to permit flow, or closed to shut the flow off, acting as an internal valve. Depending on the desired product, or the characteristics of the product, it may also be useful to widen or narrow the gap 4415, 1415 between paring disks 4410, 1410. Changing the gap affects both pumping and shear rates associated with the pairing disks.

The rate of removal of concentrate and centrate from the centrifuge 1000, and the viability of the concentrate removed, may be further controlled using a number of features of exemplary embodiments shown in FIGS. 4-13. Accelerator fins 4630, similar to those in the centrate pump chamber 1420, may be added to concentrate pump chamber 4420. The addition of accelerator fins 4630 increases the rate at which the concentrate may be removed, by overcoming some of the slow down due to friction between the moving concentrate and the paring disks 4410. In addition to accelerator fins 4630 in the upper surface of the pump chamber 4420, such fins 4630 may also be added to a lower surface in the pump chamber 4420 to increase their effectiveness. A further feature may be the substitution of slits for holes 1540, 4540, which minimizes the shear on material entering the pump chambers 1420, 4420.

If viability of the concentrate is a concern, rotatable paring disks 4410 may be included in pump chamber 4420, which reduce the shear imparted to the concentrate as it contacts the surfaces of the paring disks 4410. The rotation rate of paring disks 4410 may be adjusted to a rate somewhat between stationary and the rate of rotation of the separation chamber 1550 to balance concentrate viability against the rate of discharge. The desired angular velocity can be controlled by a number of mechanisms that are known to those skilled in the art. An example of a means of control is an external slip clutch that allows the paring disks to rotate at an angular velocity that is a fraction of that of the centrifuge. The use of slip clutches is well known to those skilled in the art. In addition, there may be means other than slip clutches to adjust the angular velocity that will be apparent to those skilled in the art.

A peristaltic pump 2510 may be also used to make removal of the concentrate more efficient and reliable, particularly with very concentrated feed suspensions. Using a peristaltic pump 2510 permits the user to more precisely control the rate of flow of the concentrate from the centrifuge 1000 than is possible relying on centripetal pumps 4400, alone, because the rate of centripetal pumps are not as easily adjustable as the rate of a peristaltic pump 2510.

In addition, a diluent, such as sterile water or a buffer, may be pumped into the concentrate pump chamber 4420 through the diluent pathway 5000 using a diluent pump 5150 in order to cut the viscosity of the concentration. A more complete discussion of useful diluents can be found above. The rate at which either or both of the peristaltic pump 2510 or the diluent pump 5150 operates may be controlled by an automated controller (not shown) responsive to a concentration sensor 4430 located in the concentrate discharge connection 2500. The controller may be programmed to start, stop, or modify the pump rate for both diluent addition and concentrate removal responsive to the particle concentration in the concentrate, either independently, responsive to a concentration sensor 4430, in conjunction with a standard feed/discharge cycle, or as a combination.

Thus the new centrifuge system and method of the present invention achieves the above stated objectives, eliminates difficulties encountered in the use of prior devices and systems, solves problems and attains the desirable results described herein.

In the foregoing description certain terms have been used for brevity, clarity and understanding, however, no unnecessary limitations are to be implied there from because such terms are for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means capable of performing the recited function, and shall not be limited to the structures shown herein or mere equivalents.

Having described the features, discoveries and principles of the invention, the manner in which it is constructed and operated, and the advantages and useful results attained, the new and useful structures, devices, elements, arrangements, parts, combinations, systems, equipment, operations and relationships are set forth in the appended claims.

What is claimed is:

1. An apparatus including structure for a centrifuge system configured to separate cells in a cell culture batch into cell concentrate and cell-free centrate, the structure comprising:
   a core structure,
      wherein the core structure is at least semi-rigid,
      wherein the core structure includes:
         a rotatable upper flange,
            wherein the upper flange includes a central opening,
         a rotatable lower flange,
         a rotatable hollow cylindrical core having an axis,
            wherein the core includes an interior,
            wherein the core includes an exterior,
            wherein the core is attached to and extends between the upper flange and the lower flange,
               wherein the interior of the core is in fluid communication with the exterior of the core;
   a rotatable flexible liner,
      wherein the liner is sealed, with respect to fluids, to the upper flange and the lower flange,
   a separation chamber,
      wherein the separation chamber is axially aligned with and surrounding the core,
      wherein the separation chamber is bounded by the flexible liner,
      wherein the separation chamber includes an outer wall,
         wherein the outer wall at least partly contains the liner,
      wherein the separation chamber includes an inner wall,
         wherein the inner wall at least partly contains the exterior of the core,
      wherein the separation chamber includes an upper end adjacent the upper flange,
      wherein the separation chamber includes a lower end adjacent the lower flange,
   feed and discharge components aligned with the axis of the core,
      wherein the feed and discharge components include a rotationally fixed central feed tube,
         wherein the feed tube includes an open lower end,
            wherein the lower end is positioned adjacent the lower flange,
         wherein during upper flange rotation, the core rotates relative to the feed tube,
      wherein the feed and discharge components include a rotationally fixed centrate discharge tube,
         wherein at least a portion of the centrate discharge tube is disposed coaxially around the feed tube, forming a hollow cylindrical conduit for centrate discharge,
         wherein during upper flange rotation, the core rotates relative to the centrate discharge tube,
      wherein the feed and discharge components include a rotationally fixed concentrate discharge tube,
         wherein at least a portion of the concentrate discharge tube is disposed coaxially around the feed tube, forming a hollow cylindrical conduit for concentrate discharge,
         wherein during upper flange rotation, the core rotates relative to the concentrate discharge tube,
   a first centripetal pump,
      wherein the first centripetal pump is rotationally fixed,
      wherein the first centripetal pump is axially aligned with the core,
      wherein the first centripetal pump is adjacent the upper flange,
      wherein during upper flange rotation, the core rotates relative to the first centripetal pump,
      wherein the first centripetal pump includes a pump chamber,
         wherein the pump chamber of the first centripetal pump is in fluid communication via at least one first passage with the separation chamber, at at least one first location that is adjacent an upper end of the inner wall of the separation chamber,
         wherein the pump chamber of the first centripetal pump is in fluid communication with the centrate discharge tube,
   a second centripetal pump,
      wherein the second centripetal pump is located higher than the first centripetal pump,
      wherein the second centripetal pump is axially aligned with the core,
      wherein the second centripetal pump includes a pump chamber,
         wherein the pump chamber of the second centripetal pump is in fluid communication via at least one second passage with the separation chamber, at at least one second location that is adjacent an upper end of the outer wall of the separation chamber,
            wherein the at least one second location is higher than the at least one first location,
         wherein the pump chamber of the second centripetal pump is in fluid communication with concentrate discharge tube.

2. The apparatus of claim 1 further having multiple use components comprising a rigid centrifuge bowl,
   wherein the upper flange operatively engages with the centrifuge bowl to provide torque to rotate the rotatable parts of the single use component,
   wherein the liner extends within and is supported by the centrifuge bowl during operation.

3. The apparatus of claim 1 wherein the lower flange includes an upper surface, and further comprising:
   a plurality of radially aligned vanes which extend orthogonally upward from the upper surface of the lower flange to the core, thereby creating a plurality of openings creating the fluid communication between the interior of the core and the exterior of the core.

4. The apparatus of claim 1 wherein the separation chamber is characterized by an upper radius and a lower radius,
   wherein the upper radius is greater than the lower radius, creating a truncated conical shape.

5. The apparatus of claim 1 wherein the pump chambers associated with each of the first and second centripetal pumps each include a pair of paring disks characterized by a radius, wherein the radius of the paring disks of the first centripetal pump is generally equal to the radius of paring disks of the second centripetal pump.

6. The apparatus of claim 1 wherein the pump chambers associated with each of the first and second centripetal pumps each include a pair of paring disks characterized by a radius,
wherein the radius of the paring disks of the first centripetal pump is less than the radius of paring disks of the second centripetal pump.

7. The apparatus of claim 1 wherein the second centripetal pump includes a plurality of accelerator vanes extending into the pump chamber of the second centripetal pump.

8. The apparatus of claim 1 wherein the feed and discharge components further include a coaxially aligned diluent feed tube,
wherein the diluent feed tube extends into and is in fluid communication with the pump chamber of the second centripetal pump.

9. The apparatus of claim 1 wherein the structure comprises single use structure for the centrifuge system.

10. The apparatus of claim 9 wherein the structure allows the centrifuge system to operate with at least one of continuous or semi-continuous discharge of cell concentrate.

11. The apparatus of claim 1 wherein the second centripetal pump is located vertically above the first centripetal pump, and wherein at least a portion of the second centripetal pump is coaxially aligned with at least a portion of the first centripetal pump.

12. The apparatus of claim 1 wherein the at least one first location is disposed radially outward further than the at least one second location.

13. An apparatus including structure for a centrifuge system configured to separate cells in a cell culture batch into cell concentrate and cell-free centrate, the structure comprising:
an upper flange, a lower flange, a hollow cylindrical core extending between the upper flange and the lower flange, a separation chamber radially surrounding the core, a feed tube, a centrate discharge tube, and a concentrate discharge tube,
wherein the upper flange is rotatable about an axis,
wherein during upper flange rotation, the upper flange rotates relative to each of the feed tube, the centrate discharge tube, and the concentrate discharge tube,
a centripetal centrate pump,
wherein the centrate pump includes a pair of paring discs,
wherein the centrate pump is axially aligned with the core,
wherein the centrate pump is disposed coaxially about the feed tube,
wherein the centrate pump includes a centrate pump chamber,
wherein the centrate pump chamber is in fluid communication with the separation chamber,
wherein the centrate pump chamber is in fluid communication with the centrate discharge tube,
wherein during upper flange rotation, the upper flange rotates relative to the centrate pump,
a centripetal concentrate pump,
wherein the concentrate pump includes a pair of paring discs,
wherein the concentrate pump is axially aligned with the core,
wherein the concentrate pump is disposed coaxially about the feed tube,
wherein the concentrate pump includes a concentrate pump chamber,
wherein the concentrate pump chamber is in fluid communication with the separation chamber,
wherein the concentrate pump chamber is in fluid communication with the concentrate discharge tube,
wherein the concentrate pump chamber includes a plurality of accelerator fins,
wherein the accelerator fins are configured to transmit angular rotation to concentrate in the concentrate pump chamber,
wherein the concentrate pump is located above the centrate centripetal pump.

14. The apparatus of claim 13 wherein the concentrate pump chamber includes accelerator fins located above the paring discs of the concentrate pump.

15. The apparatus of claim 14 wherein the centrate pump chamber includes a plurality of accelerator fins,
wherein the accelerator fins of the centrate pump chamber are configured to transmit angular rotation to centrate in the centrate pump chamber.

16. The apparatus of claim 15 wherein the centrate pump chamber includes accelerator fins located above the paring discs of the centrate pump.

17. An apparatus including structure for a centrifuge system configured to separate cells in a cell culture batch into cell concentrate and cell-free centrate, the structure comprising:
a feed tube, a centrate discharge tube, and a concentrate discharge tube,
a rotatable upper flange,
wherein the upper flange includes a central opening,
wherein the upper flange is rotatable about an axis,
wherein during upper flange rotation, the upper flange rotates relative to each of the feed tube, the centrate discharge tube, and the concentrate discharge tube,
a rotatable lower flange,
wherein the lower flange includes an upper conical surface,
a rotatable hollow cylindrical core,
wherein the core includes a core interior,
wherein the core is rotatable about the axis,
a flexible liner,
wherein the liner is connected to the upper flange and the lower flange,
a separation chamber,
wherein the separation chamber is axially aligned with and surrounds the core,
wherein the separation chamber is bounded by an inner wall and an outer wall,
wherein the separation chamber is in fluid communication with the core interior,
annularly arranged accelerator vanes,
wherein each vane extends orthogonally upward from the upper conical surface of the lower flange,
wherein each vane extends in a radially outward direction,
wherein the vanes are configured to impart an angular velocity to feed
suspension being moved from the core interior to the separation chamber,
wherein during lower flange rotation, the angular velocity imparted approaches angular velocity of the lower flange,
a first centripetal pump,
wherein the first centripetal pump includes a pump chamber, wherein the pump chamber of the first centripetal pump is in fluid communication with the separation chamber at an upper end of the inner wall, wherein the pump chamber of the first centripetal pump is in fluid communication with the centrate discharge tube, wherein during upper flange rotation, the core rotates relative to the first centripetal pump, a second centripetal pump, wherein the second centripetal pump is located above the first centripetal pump, wherein the second centripetal pump includes a pump chamber, wherein the pump chamber of the second centripetal pump is in fluid communication with the separation chamber at an upper end of the outer wall, wherein the pump chamber of the second centripetal pump is in fluid communication with concentrate discharge tube.

18. The apparatus of claim 17 wherein the upper end of the outer wall is higher positioned than the upper end of the inner wall.

19. The apparatus of claim 17 wherein the separation chamber is characterized by an upper radius and a lower radius, wherein the upper radius is greater than the lower radius, creating a truncated conical configuration.

20. The apparatus of claim 17 wherein the pump chamber of the second centripetal pump includes a plurality of accelerator fins, wherein the accelerator fins are configured to transmit angular rotation to concentrate in the pump chamber of the second centripetal pump.

\* \* \* \* \*